United States Patent
Savage

(10) Patent No.: US 10,959,433 B2
(45) Date of Patent: Mar. 30, 2021

(54) USE OF CATIONIC STEROIDAL ANTIMICROBIALS FOR SPORICIDAL ACTIVITY

(71) Applicant: Paul B. Savage, Mapleton, UT (US)

(72) Inventor: Paul B. Savage, Mapleton, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 122 days.

(21) Appl. No.: 15/926,534

(22) Filed: Mar. 20, 2018

(65) Prior Publication Data

US 2018/0271100 A1     Sep. 27, 2018

Related U.S. Application Data

(60) Provisional application No. 62/474,495, filed on Mar. 21, 2017.

(51) Int. Cl.
| | | |
|---|---|---|
| *A01N 45/00* | (2006.01) | |
| *A61L 2/18* | (2006.01) | |
| *A61P 31/04* | (2006.01) | |
| *A01N 55/00* | (2006.01) | |
| *A01N 55/08* | (2006.01) | |
| *A01N 47/44* | (2006.01) | |
| *A01N 47/28* | (2006.01) | |

(52) U.S. Cl.
CPC ............. *A01N 45/00* (2013.01); *A01N 47/28* (2013.01); *A01N 47/44* (2013.01); *A01N 55/00* (2013.01); *A01N 55/08* (2013.01); *A61L 2/18* (2013.01); *A61P 31/04* (2018.01); *A61L 2202/24* (2013.01)

(58) Field of Classification Search
CPC ........ A01N 45/00; A01N 55/00; A01N 55/08; A01N 47/44; A01N 47/28; A61L 2/18; A61L 2202/24; A61P 31/04
See application file for complete search history.

(56) References Cited

U.S. PATENT DOCUMENTS

| | | | |
|---|---|---|---|
| 821,187 | A | 5/1906 | Peters |
| 3,843,779 | A | 10/1974 | Norfleet |
| 4,248,236 | A | 2/1981 | Linder |

(Continued)

FOREIGN PATENT DOCUMENTS

| | | |
|---|---|---|
| CA | 2322847 A1 | 9/1999 |
| CA | 2842460 A1 | 1/2013 |

(Continued)

OTHER PUBLICATIONS

U.S. Appl. No. 15/895,848, filed Feb. 13, 2018, Genberg, et al.

(Continued)

*Primary Examiner* — Regina M Yoo
(74) *Attorney, Agent, or Firm* — Workman Nydegger

(57) ABSTRACT

This disclosure relates to sporicidal compositions and uses thereof. The sporicidal compositions include one or more cationic steroidal antimicrobials (CSAs). The sporicidal compositions may be applied to an object to kill or deactivate bacterial spores contacting the sporicidal composition. The object may be a food product, food processing equipment, industrial equipment, or healthcare facility objects. The sporicidal composition may be administered to a subject that has, is suspected to have, or is at risk for an infection associated with spore-forming bacteria.

19 Claims, 20 Drawing Sheets

(56) References Cited

U.S. PATENT DOCUMENTS

| | | |
|---|---|---|
| 4,284,236 A | 8/1981 | Bradshaw |
| 4,289,755 A | 9/1981 | Dhabhar |
| 4,296,206 A | 10/1981 | Simons |
| 4,473,988 A | 10/1984 | Scott |
| 4,661,341 A | 4/1987 | Benedict et al. |
| 4,723,950 A | 2/1988 | Lee |
| 4,765,855 A | 8/1988 | Geoffroy-Dechaume et al. |
| 4,842,593 A | 6/1989 | Jordan et al. |
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,352,682 A | 10/1994 | Sipos |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,687,714 A | 11/1997 | Kolobow |
| 5,721,359 A | 2/1998 | Dunn et al. |
| 5,763,430 A | 6/1998 | Zasloff |
| 5,919,183 A | 7/1999 | Field |
| 6,117,332 A | 9/2000 | Hatch et al. |
| 6,217,896 B1 | 4/2001 | Benjamin |
| 6,228,393 B1 | 5/2001 | DiCosmo et al. |
| 6,329,488 B1 | 12/2001 | Terry et al. |
| 6,344,184 B1 | 2/2002 | Rolla |
| 6,350,738 B1 | 2/2002 | Savage et al. |
| 6,486,148 B2 | 11/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,767,904 B2 | 7/2004 | Savage et al. |
| 6,773,717 B1 | 8/2004 | Winstrom |
| 6,803,030 B2 | 10/2004 | De et al. |
| 6,803,066 B2 | 10/2004 | Traeder |
| 6,872,303 B2 | 3/2005 | Knapp et al. |
| 6,872,306 B2 | 3/2005 | Shen |
| 6,939,376 B2 | 7/2005 | Shulze et al. |
| 7,226,577 B2 | 6/2007 | Cappelletti et al. |
| 7,235,552 B1 | 6/2007 | Hesse et al. |
| 7,282,214 B2 | 10/2007 | Wilcox et al. |
| 7,381,439 B2 | 6/2008 | Hilgren et al. |
| 7,481,973 B2 * | 1/2009 | Beilfuss ................ A01N 31/02 422/28 |
| 7,598,234 B2 | 10/2009 | Savage et al. |
| 7,611,692 B2 | 11/2009 | Cappelletti et al. |
| 7,659,061 B2 | 2/2010 | Hendl et al. |
| 7,754,705 B2 | 7/2010 | Savage et al. |
| 7,850,947 B2 | 12/2010 | Cappelletti et al. |
| 7,854,941 B2 | 12/2010 | Urban et al. |
| 7,993,903 B2 | 8/2011 | Hayakawa et al. |
| 7,999,390 B2 | 8/2011 | Ishigaki et al. |
| 8,211,879 B2 | 7/2012 | Savage et al. |
| 8,420,050 B2 | 4/2013 | Cappelletti et al. |
| 8,444,954 B2 | 5/2013 | Cappelletti et al. |
| 8,529,681 B1 | 9/2013 | Hibbs et al. |
| 8,530,002 B1 | 9/2013 | Hibbs et al. |
| 8,557,031 B1 | 10/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 8,787,857 B2 | 7/2014 | Ezaki |
| 8,932,614 B2 | 1/2015 | Savage et al. |
| 8,945,217 B2 | 2/2015 | Savage et al. |
| 8,975,310 B2 | 3/2015 | Savage |
| 9,155,746 B2 | 10/2015 | Genberg et al. |
| 9,161,942 B2 | 10/2015 | Genberg et al. |
| 9,314,472 B2 | 4/2016 | Beus et al. |
| 9,345,655 B2 | 5/2016 | Vazquez et al. |
| 9,387,215 B2 | 7/2016 | Beus et al. |
| 9,434,759 B1 | 9/2016 | Savage |
| 9,527,883 B2 | 12/2016 | Savage et al. |
| 9,533,063 B1 * | 1/2017 | Savage ................ A01N 45/00 |
| 9,546,195 B2 | 1/2017 | Savage |
| 9,603,859 B2 | 3/2017 | Genberg et al. |
| 10,568,893 B2 | 2/2020 | Savage et al. |
| 2002/0019376 A1 | 2/2002 | Savage et al. |
| 2002/0091278 A1 | 7/2002 | Savage et al. |
| 2002/0091433 A1 | 7/2002 | Ding et al. |
| 2003/0018306 A1 | 1/2003 | Bucay-Couto et al. |
| 2003/0099717 A1 | 5/2003 | Cabrera |
| 2003/0170354 A1 | 9/2003 | Beelman et al. |
| 2003/0232791 A1 | 12/2003 | Levitt et al. |
| 2004/0009227 A1 | 1/2004 | Yao |
| 2004/0011358 A1 | 1/2004 | Smaldone et al. |
| 2004/0018154 A1 | 1/2004 | Pan |
| 2004/0058974 A1 | 3/2004 | Courtney et al. |
| 2004/0071781 A1 | 4/2004 | Chattopadhyay et al. |
| 2004/0126409 A1 | 7/2004 | Wilcox et al. |
| 2004/0134292 A1 | 7/2004 | Roth |
| 2004/0170563 A1 | 9/2004 | Meade |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0014738 A1 | 1/2006 | Wachendorff-neumann et al. |
| 2006/0062742 A1 | 3/2006 | Davis et al. |
| 2006/0269485 A1 | 11/2006 | Friedman et al. |
| 2007/0053788 A1 | 3/2007 | Zhao |
| 2007/0077292 A1 | 4/2007 | Pinsky |
| 2007/0106393 A1 | 5/2007 | Miles et al. |
| 2007/0134292 A1 | 6/2007 | Suokas et al. |
| 2007/0154554 A1 | 7/2007 | Burgermeister et al. |
| 2007/0170563 A1 | 7/2007 | Chen |
| 2007/0190066 A1 | 8/2007 | Savage et al. |
| 2007/0190067 A1 | 8/2007 | Savage et al. |
| 2007/0190558 A1 | 8/2007 | Savage et al. |
| 2007/0243225 A1 | 10/2007 | McKay |
| 2007/0269375 A1 | 11/2007 | Chen et al. |
| 2008/0085949 A1 | 4/2008 | McGhee |
| 2008/0124376 A1 | 5/2008 | Pruitt et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0024101 A1 | 1/2009 | Toshishige et al. |
| 2009/0054295 A1 | 2/2009 | Vicari et al. |
| 2009/0068122 A1 | 3/2009 | Pilch et al. |
| 2009/0099531 A1 | 4/2009 | Griesbach, III |
| 2009/0226884 A1 | 9/2009 | Tsujimoto et al. |
| 2009/0252781 A1 | 10/2009 | Sawhney et al. |
| 2009/0279944 A1 | 11/2009 | Schmitz et al. |
| 2009/0324517 A1 | 12/2009 | Kline |
| 2010/0022481 A1 | 1/2010 | Wang et al. |
| 2010/0092398 A1 | 4/2010 | Reynolds |
| 2010/0209497 A1 | 8/2010 | Thornthwaite |
| 2010/0226884 A1 | 9/2010 | Chang et al. |
| 2010/0310478 A1 | 12/2010 | Fitzgerald et al. |
| 2010/0330086 A1 | 12/2010 | Savage et al. |
| 2011/0033540 A1 | 2/2011 | Daniloff et al. |
| 2011/0091376 A1 | 4/2011 | Savage |
| 2011/0123624 A1 | 5/2011 | Zasloff |
| 2011/0135742 A1 | 6/2011 | Kim et al. |
| 2011/0171144 A1 | 7/2011 | Wang et al. |
| 2011/0230589 A1 | 9/2011 | Maggio et al. |
| 2012/0088733 A1 | 4/2012 | Kim et al. |
| 2012/0107382 A1 | 5/2012 | Savage |
| 2012/0128793 A1 | 5/2012 | Miller et al. |
| 2013/0004586 A1 | 1/2013 | Vachon |
| 2013/0022651 A1 * | 1/2013 | Savage ................ A61L 29/16 424/400 |
| 2013/0034500 A1 | 2/2013 | Savage et al. |
| 2013/0040265 A1 | 2/2013 | Park et al. |
| 2013/0053507 A1 | 2/2013 | Savage |
| 2013/0089580 A1 | 4/2013 | Boutros |
| 2013/0137668 A1 | 5/2013 | Fein et al. |
| 2013/0234842 A1 | 9/2013 | Leitz |
| 2013/0236619 A1 | 9/2013 | Savage |
| 2013/0243823 A1 | 9/2013 | Genberg et al. |
| 2013/0243840 A1 | 9/2013 | Savage et al. |
| 2013/0243842 A1 | 9/2013 | Genberg et al. |

(56) References Cited

U.S. PATENT DOCUMENTS

| | | |
|---|---|---|
| 2013/0245760 A1 | 9/2013 | Savage et al. |
| 2013/0280312 A1 | 10/2013 | De Szalay |
| 2013/0280391 A1 | 10/2013 | Savage |
| 2014/0062960 A1 | 3/2014 | Kim et al. |
| 2014/0107090 A1 | 4/2014 | Beus et al. |
| 2014/0194401 A1* | 7/2014 | Genberg ............... A61K 31/575 514/182 |
| 2014/0219914 A1 | 8/2014 | Govindan et al. |
| 2014/0228905 A1 | 8/2014 | Bolea |
| 2014/0271761 A1 | 9/2014 | Savage et al. |
| 2014/0274913 A1 | 9/2014 | Savage et al. |
| 2014/0305461 A1 | 10/2014 | Pimenta et al. |
| 2014/0315873 A1 | 10/2014 | Beus et al. |
| 2014/0336131 A1 | 11/2014 | Savage et al. |
| 2014/0363780 A1 | 12/2014 | Vazquez et al. |
| 2014/0369941 A1 | 12/2014 | Vazquez et al. |
| 2015/0093423 A1 | 4/2015 | Savage et al. |
| 2015/0110767 A1 | 4/2015 | Savage et al. |
| 2015/0314342 A1 | 4/2015 | Beus et al. |
| 2015/0140063 A1 | 5/2015 | Savage |
| 2015/0374719 A1 | 6/2015 | Genberg et al. |
| 2015/0203257 A1 | 7/2015 | Canegallo |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |
| 2015/0366880 A1 | 9/2015 | Genberg et al. |
| 2015/0374720 A1 | 12/2015 | Genberg et al. |
| 2016/0193232 A1 | 3/2016 | Beus et al. |
| 2016/0199390 A1 | 3/2016 | Beus et al. |
| 2016/0052959 A1 | 8/2016 | Savage |
| 2016/0022702 A1 | 10/2016 | Savage et al. |
| 2016/0045421 A1 | 10/2016 | Vazquez et al. |
| 2016/0096864 A1 | 10/2016 | Savage |
| 2016/0311850 A1 | 10/2016 | Savage et al. |
| 2016/0311851 A1 | 10/2016 | Savage et al. |
| 2017/0035677 A1 | 2/2017 | Vazquez et al. |
| 2017/0080128 A1 | 3/2017 | Genberg et al. |
| 2017/0137459 A1* | 5/2017 | Savage .................. A61P 31/00 |
| 2017/0210776 A1 | 7/2017 | Savage |
| 2017/0232004 A1 | 8/2017 | Savage et al. |
| 2017/0258963 A1 | 9/2017 | Savage et al. |
| 2018/0164221 A1* | 6/2018 | Singh ................. A61B 5/4238 |
| 2018/0280550 A1 | 10/2018 | Savage |
| 2019/0076581 A1 | 3/2019 | Savage et al. |

FOREIGN PATENT DOCUMENTS

| | | |
|---|---|---|
| CN | 101378761 | 3/2009 |
| CN | 102145005 | 8/2011 |
| CN | 102172356 | 9/2011 |
| DE | 1037074 | 8/1958 |
| EP | 0341951 | 11/1989 |
| EP | 1208844 | 5/2002 |
| EP | 1219631 | 7/2002 |
| EP | 1250849 A1 | 10/2002 |
| EP | 1058552 B1 | 6/2004 |
| EP | 1311531 B1 | 5/2016 |
| JP | 02014741 | 1/1990 |
| JP | H0474026 | 11/1992 |
| JP | 06153779 | 6/1994 |
| JP | 07501826 | 2/1995 |
| JP | 09248454 | 9/1997 |
| JP | 2002505292 | 2/2002 |
| JP | 2002255771 | 9/2002 |
| JP | 2002534532 | 10/2002 |
| JP | 2002538093 | 11/2002 |
| JP | 2004-506599 A | 3/2004 |
| JP | 2004506645 | 3/2004 |
| JP | 2010-059194 A | 3/2010 |
| JP | 2010533051 | 10/2010 |
| JP | 2010538074 | 12/2010 |
| JP | 2011527702 | 11/2011 |
| JP | 2014500741 | 1/2014 |
| WO | 93/01829 A1 | 2/1993 |
| WO | 1995024415 | 9/1995 |
| WO | 98/05337 A1 | 2/1998 |
| WO | 9827106 | 6/1998 |
| WO | 99/45024 A1 | 9/1999 |
| WO | 1999044616 | 9/1999 |
| WO | 2000042058 | 7/2000 |
| WO | 2002014342 | 2/2002 |
| WO | 2002067979 | 9/2002 |
| WO | 2003015757 | 2/2003 |
| WO | 03/66119 | 8/2003 |
| WO | 03090799 | 11/2003 |
| WO | 2004082588 | 9/2004 |
| WO | 2004112852 | 12/2004 |
| WO | 2007089903 | 8/2007 |
| WO | 2007089906 | 8/2007 |
| WO | 2007089907 | 8/2007 |
| WO | 2007134176 | 11/2007 |
| WO | 2008038965 | 4/2008 |
| WO | 2008048340 | 4/2008 |
| WO | WO2008096149 | 8/2008 |
| WO | 2009049370 | 4/2009 |
| WO | 2009079066 | 6/2009 |
| WO | 2009144708 | 12/2009 |
| WO | 2010006192 | 1/2010 |
| WO | 2010036427 | 4/2010 |
| WO | 2010062562 | 6/2010 |
| WO | 2011066260 | 6/2011 |
| WO | 2011109704 | 9/2011 |
| WO | 2012061651 | 5/2012 |
| WO | 2013/013221 A1 | 1/2013 |
| WO | 2013/013223 A1 | 1/2013 |
| WO | 2013029055 | 2/2013 |
| WO | 2013029059 | 2/2013 |
| WO | 2013/040265 A1 | 3/2013 |
| WO | 2013040269 | 3/2013 |
| WO | WO2013131060 | 6/2013 |
| WO | 2013109236 | 7/2013 |
| WO | 2013167743 | 11/2013 |
| WO | 2014062960 | 4/2014 |
| WO | 2014/107740 A2 | 7/2014 |
| WO | WO 2014151411 | 9/2014 |
| WO | WO2015058087 | 4/2015 |
| WO | 2015/138716 A2 | 9/2015 |
| WO | WO2015200815 | 12/2015 |
| WO | WO2016172543 | 10/2016 |
| WO | 2016186821 | 11/2016 |
| WO | 2017/053355 A1 | 3/2017 |

OTHER PUBLICATIONS

U.S. Appl. No. 15/926,577, filed Mar. 20, 2018, Savage et al.
U.S. Appl. No. 15/934,534, filed Mar. 23, 2018, Savage.
Alafort et al., "Lys and Arg in UBI: A specific site for a stable Tc-99m complex?", Nuclear Medicine and Biology 30 (2003) 605-615.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Basf, Pluronic® Block Copolymer NF Grades (Poloxamer NF Grades), Technical Bulletive (2004).
Bakri et al., "Inhibitory effect of garlic extract on oral bacteria", Archives of Oral Biology, 50: 645-651.
Bellini et al., "Cholic and deoxycholic acids derivatives (Part I). Antimicrobial activity of cholane compounds", European J. of Medicinal Chem., 18(2), pp. 185-190, 1983.
Belikov V.G., Pharmaceutical Chemistry, M., Higher School, 1993, p. 43-47.
Bellini et al., "Cholic and deoxycholic acids derivatives (Part II). Antimicrobial activity of cholane compounds", European J. of Medicinal Chem., 18(2), pp. 191-195, 1983.

(56) References Cited

OTHER PUBLICATIONS

Berge et al., "Pharmaceutical Salts", Journal of Pharmaceutical Sciences, Jan. 1977, vol. 66, No. 1, pp. 1-19.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.
Britton et al, "Imaging bacterial infection with 99mTc-ciprofloxacin (Infection)", Journal of Clinical Pathology, vol. 55, pp. 817-823, Apr. 6, 2015.
Brown, "Bioisosteres in Medicinal Chemistry, First Edition", edited by Nathan Brown, 2012, Ch. 2 Classical Bioisosteres, pp. 1-52.
Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.
Bucki et al., "Resistance of the antibacterial agent ceragenin CSA-13 to inactivation by DNA or F-actin and its activity in cystic fibrosis sputum", Journal of Antimicrobial Chemotherapy (2007) 60: 535-545, 11 pages.
Bush, "Staphylococcal Infections", Merck Manuals Professional Edition, http://www.merckmanuals.com/professional/infectious-diseases/gram-positive-cocci/staphylococcal-infections.
Chin et al, "Antimicrobial Activities of Ceragenins against Clinical Isolates of Resistant *Staphylococcus aureas*.", Antimicrobial Agents and Chemotherapy, vol. 51, No. 4, Apr. 2007, p. 1268-1273.
Cipolla et al., "Inhaled antibiotics to treat lung infection", Pharm Pat Anal., Sep. 2013.
Clara et al., "Preclinical evaluation of magainin-A as a contraceptive antimicrobial agent", Fertility and Sterility 81 (5), pp. 1357-1365, 2004.
De Cuyper et al., "Surface functionalization of magnetoliposomes in view of improving iron oxide-based magnetic resonance imaging contrast agents: Anchoring of gadolinium ions to a lipophilic chelate", 2007 Anal. Biochem. 367: 266-273. Published online May 10, 2007.
Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Dörwald, "Side Reactions in Organic Synthesis", 2005, Wiley-VCH Verlag GmbH & Co., KGaA, Weinhelm, Preface. p. IX.
Elder et al., "The Utility of Sulfonate Salts in Drug Development", Journal of Pharmaceutical Sciences 99(7): 2948-2961.
Epand et al., "Bacterial lipid composition and the antimicrobial efficacy of cationic steroid compounds (Ceragenins)", BBA, 2007, pp. 65-78.
Erskine et al., "Mastitis in Cattle", Merck Manual: Veterinary Manual. Electronic Resource: [http://www.merckvetmanual.com/reproductive-system/mastitis-in-large-animals/mastitis-in-cattle], retrieved Mar. 8, 2017.
Fichna et al., "Synthesis of Target-Specific Radiolabeled Peptides for Diagnostic Imaging", Bioconjugate Chem., 2003, 14, 3-17, American Chemical Society.
Food definition, Merriam Webster, https://www.merriam-webster.com/dictionary/food, Accessed Feb. 12, 2018.
Fritsch et al, "In Vitro Activity of Nine Developmental Cationic Steroid Compounds (Ceragenins) against Clinical Isolates of Clostridium difficile", The 46th Interscience Conference on Antimicrobial Agents and Chemotherapy, Sep. 27, 2006, pp. 1-1.
Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.
Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/010062704/suppl file/o10062704 sl.pdf.
Howell, et al., "Ceragenins: A 1-18, class of Antiviral Compounds to Treat Orthopox Infections", Journal of Investigative Dermatology, vol. 129, No. 11, Jun. 11, 2009, pp. 2688-2675.
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
International Search Report for PCT Application No. PCT/US2011/059225 dated Jan. 31, 2012.
International Search Report for PCT Application No. PCT/US2012/047750, dated Oct. 5, 2012, Filed Date: Sep. 27, 2012, 3 pages.
International Search Report for PCT Application No. PCT/US2012/055244 dated Dec. 5, 2012.
International Search Report for PCT Application No. PCT/US2012/055248 dated Feb. 14, 2013.
International Search Report for PCT Application No. PCT/US2013/038090, dated Jul. 24, 2013.
International Search Report for PCT Application No. PCT/US2014/034986 dated Aug. 28, 2014.
International Search Report for PCT Application No. PCT/US2013/065510, dated Apr. 30, 2015.
International Search Report for PCT Application No. PCT/US2015/020166 dated Sep. 2, 2015.
International Search Report for PCT Application No. PCT/US2015/038029 dated Sep. 29, 2015.
International Search Report for PCT Application No. PCT/US2015/046412 dated Dec. 1, 2015.
International Search Report for PCT Application No. PCT/US2015/054434 dated Dec. 23, 2015.
International Search Report for PCT Application No. PCT/US2016/052771 dated Dec. 9, 2016.
Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.
Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
Lai, et al., "Controlled Released of a Bactericidal Ceragenin-Polymer Conjugate", Sep. 227, 2006, p. 1, 46th Annual Interscience Conference on Antimicrobial Agents and Chemotherapy.
Lankinen et al., "Ga-Dota-Peptide Targeting VAP-1 for In Vivo Evaluation of Inflammatory and Infectious Bone Conditions", 52nd Annual Meeting of the Orthopaedic Research Society.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
K. Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.
Li et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.
Li et al., "Incremental conversion of Outer-Membrane Permeabilizers into Potent Antibiotics for Gram-Negative Bacteria", J. Am. Chem. Soc. 1999, 121, 931-940.

(56) References Cited

OTHER PUBLICATIONS

Lowe et al., "Effect of Hydrophobicity of a Drug on its Release from Hydrogels with Different Topological Structures" Journal of Polymer Science (1999) 73: 1031-1039 (9 pages).

Martin, L., WebMD, 2012, pp. 1-25.

Massoud et al., "Molecular imaging in living subjects: seeing fundamental biological processes in a new light", Genes & Development 17: 545-580 2003, Cold Spring Harbor Laboratory Press.

Novy et al., "Infections as a Cuase of Infertility", Glob. Libr. Women's med., (ISSN: 1756-2228) 2008; DOI 10.3843/GLOWM.10328.

Papo et al., "Host peptides as new weapons in cancer treatment", CMLS Cell. Mol. Life Sci. 62 (2005), 784-790.

Emily L. Perry et al., "Assessing peri-implant tissue infection prevention in a percutaneous model", Journal of Biomedical Materials Research Part B: Applied Biomaterials, vol. 02B, Nov. 19, 2009, pp. 397-408.

Piktel et al. Sporicidal Activity of Ceragenin CSA-13 Against Bacillus subtillis, Scientific Reports, vol. 7, Mar. 15, 2017 [retrieved on Apr. 24, 2018. Retreived from the internet: <URL: https://www.nature.com/articles/srep44452.pdf> Entire Document.

Pitten F-A, et al., "Efficacy of cetylpyridinium chloride used as oropharyngeal antiseptic" Arzenimittel Forschung. Rug Research, ECV Editio Cantor Verlag, Aulendorf, DE, vol. 51, No. 7, Jan. 1, 2001, pp. 588-595.

Polat et al., "In Vitro Amoebicidal Activity of a Ceragenin, Cationic Steroid Antibiotic-13, Against Acanthamoeba castellanii and Its Cytotoxic Potential", Journal of Ocular Pharmacology and Therapeutics, vol. 27, No. 1, 2011.

Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of *Pseudomonas*, Denver, CO—Published Dec. 20, 2007).

Pycock, "The Dirty Mare", https://www.equine-reproduction.com/articles/DirtyMare.shtml, 2003.

Roohi et al., Prepration, quality control and biological evaluation of 99m-Tc-labelled cationic steroid antibiotic (CSA-13), Radiochim. Acta 197, 57-62 (2009).

Savage, et al., "Antibacterial Activities of Thin Films Containing Ceragenins", Microbial Surfaces: Structure, Interactions and Reactivity, ACS, May 30, 2008, pp. 65-78.

Paul B. Savage, et al: "Antibacterial Properties of cationic steroid antibiotics", FEMS Microbiology Letters, vol. 217, Nov. 2002, pp. 1-7.

P. B. Savage, et al., "Thin Films Containing Ceragenins Prevent Biofilm Formation on Endotracheal Tubes", 9th International Federation of Infection Control Congress, Oct. 14, 2008, pp. 1-1.

P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.

Schmidmaier et al., "Local Application of Growth Factors (Insulin-Like Growth Factor-1 and Transforming Growth Factor-β1) From a Biodegradable Poly(D, L-lactide) Coating of Osteosynthetic Implants Accelerates Fracture Healing in Rats", Bone vol. 28 No. 4, Apr. 2001.

Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).

K.D. Sinclair, et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.

Steeneveld, et al., "Cow-specific treatment of clinical mastitis: an economic approach", Journal of Dairy Science vol. 94, Jan. 2011, pp. 174-188.

Survey Research on Behcet's Disease, 2005 to 2007 Comprehensive Survey Reports, 2008, pp. 34-39.

Suzuki et al., "Molecular Genetics of Plant Sterol Backbone Synthesis", 2007; Lipids; 42: 47-54.

Van Bambeke et al: "The bacterial envelope as a target for novel anti-MRSA antibiotics", Trends in Pharmaceutical Sciences, Elsevier, Haywarth, GB, vol. 29, No. 3, Feb. 11, 2008 (Feb. 11, 2008), pp. 124-134.

Van Den Bogaard et al., "Antibiotic Usage in Animals: Impact on Bacterial Resistance and Public Health"; 1999; Drugs; 58 (4): 589-607.

Welling et al., "Radiochemical and biological characteristics of 99m-Tc-UBI 29-41 for imaging of bacterial infections", Nuclear Medicine and Biology 29 (2002) 413-422.

Willemen et al., "Miceli Formation and Antimicrobial Acivity of Cholic Acid Derivatives with three Permanent Ionic Head Groups", Angew. Chem. Int. Ed., 2002, 41, No. 22.

Williams et al., "In vivo efficacy of a silicone-cationic steroid antimicrobial coating to prevent implant-related infection", Biomaterials, Nov. 2012: 33(33): 8641-8656 (Department of Brigham Young University).

Winter et al., "Improved paragmentic chelate for molecular imaging with MRI", 2005 J. Magn. Magn. Mater. 293: 540-545.

Wu et al., "Biodegradable hydrophobic-hydrophilic hybrid hydrogels: swelling behavior and controlled drug release", Journal of Biomaterials Science Polymer Edition (J. Biomatter. Sci. Polymer Ed.) (2008) 19 (4): 411-429 (20 pages, including copyright information).

Xin-Zhong Lai, et al., "Ceragenins: Cholic Acid-Based Mimics of Antimicrobial peptides", Account of Chemical Research vol. 41, No. 10, Oct. 21, 2008, pp. 1233-1240.

Melinda Yin, et al., "Antiangiogenic Treatment Delays Chondrocyte Maturation and Cone Formation During Lim Skeletogenesis", Journal of Vone and Mineral Research, American Society for Bone and Mineral Research, New York, NY, US, vol. 17, No. 1, Jan. 1, 2002.

Zanger et al., "Structure-Activity Relationship and Drug Design", Remington's Pharmaceutical Sciences, Chapter 27, 16th Edition, 1980, pp. 420-425.

Kuroda, et al., "Ceragenin CSA-13 induces cell cycle arrest and antiproliferative effects in wild-type and p52 null mutant HCT116 colon cancer cells", Preclinical Report, Wolters Kluwer Health 2013.

Weijian Ye et al "Synthesis and antibacterial activity of new long-chain-alkyl bile acid-based amphiphiles", Bioorganic Chemistry, vol. 51, Aug. 19, 2013, pp. 1-7, XP55513451, US ISSN: 0045-2068, DOI:10.1013/j.bioorg.2013.08.003.

"Quaternary Ammoniuim Compounds", Van Nostrand's Scientific Encyclopedia, Jan. 1, 2006, John Wiley & Sons, Inc.

Opsenica D, et al., "Cholic Acid Derivatives as 1,2,4,5-Tetraoxane Carriers: Structure and Antimalarial and Antiproliferative Activity", J. Med Chem. Aug. 2000.

Valkonen, et al., "Bile acid amidoalcohols: simple organogelators", Biosens Bioelectron, Dec. 2004.

Deepak B. Salunke et al., "Amino Functionalized Novel Cholic Acid Derivatives Induce HIV-1 Replication and Syncytia Formation in T Cells", J. Med. Chem. 2006.

Ding, et al., "Correlation of the Antibacerial Activities of Cationic Peptid Antibiotics and Cationic Steroid Antibiotics", J. Med. Chem., vol. 45, pp. 663-669 (Year: 2002).

International Search Report for PCT Application No. PCT/US2018/023566 dated Mar. 21, 2018.

Uncategorized: CSA Biotechnologies LLC, Apr. 5, 2011.

"Martindale: the complete drug reference, Cetrimide; Cetylpyridinium chloride ED-PARFITT K", Jan. 1, 2000, pp. 1105-1106.

Barton, Journal of Clinical Investigation, vol. 118, No. 2, Feb. 2008, Review Series, pp. 413-420.

Feng, Theses Brigham Young University, BYU Scholars Archive, dated Dec. 19, 2011, 892.

Chen et al, J Drug Target, Dec. 2012; 20(10):856-63, 892.

Ogata et al. Intramammary application of ozone therapy to acute clinical mastitis in dairy cows. J. Vet. Med. Sci. 62(7): 681-686, 2000.

De Haas et al. Associations between pathogen-specific cases of clinical mastitis and somatic cell count patterns. J. Dairy Sci. 87: 95-105.

(56) References Cited

OTHER PUBLICATIONS

Dennison et al., "Anticancer a—Helical Peptides and Structure/Function Relationships Underpinning their Interactions with Tumour Cell Membranes", Current Protein and Peptide Science, 2006, 7, No. 6, pp. 1-13.
Ding, et al., "Origins of cell selectivity of cationic steroid antibiotics", Journal of American Chemical Society, Oct. 2004, pp. 13642-13648.
International Search Report and Written Opinion received for PCT Patent Application No. PCT/US2020/034297, dated Aug. 26, 2020, 8 pages.
Papo et al., "Host defense peptides as new weapons in cancer treatment", Cmls Cellular and Molecular Life Sciences, vol. 62, No. 7-8, Apr. 1, 2005, pp. 784-790.
"Mouth rinse" definition by Medical dictionay. Retrieved from http://medical-dictionary.thefreedictionary.com/mouth-i-rinse.
Ahmed, Hydrogel: Preparation, characterization, and applications: A review, Journal of Advanced Research (2015) 6: 105-121 (Year: 2015).
Bondaryk et al. Postep. Derm. Alergol., 2013, vol. 5, pp. 293-301.
Czernomysy-Furowicz et al. Etiological agents of mastitis in dairy cows on a farm in the West Pomeranian Region. Acta Sci. Pol., Zootechnica 7(1) 2008, 3-10.
Dean et al.; Flavor Associated with Fish Meal in Diets Fed to Broiler Chickens; 1968; Can. J. Animal Sci.; 49:11-15 (Year: 1968).
Dumortier, Getal. (Pharmaceutical Research, vol. 23, No. 12, Dec. 2006).
International Search Report for PCT Application No. PCT/US2009/047485 dated Feb. 17, 2010.
Jacob; Feeding Fishmeal to Poultry; https://articles.extension.org/pages/67357/feeding-fishmeal-to-poultry; May 5, 2015; accessed Sep. 10, 2018 (Year: 2015).
Kaltsas et al., Endocrine-Related Cancer (2005) 12 683-699.
Leszczynska et al. (J Antimicrob Chemother, published Nov. 7, 2012), Bacterial activity of cationic lipids, pp. 1-9).
Louw et al., "Recueil des Travaux Chimiques des Pays-Bas et la Belgique", vol. 73, pp. 667-676, 1954.
Munoz-Juarez et al., "Wide-Lumen Stapled Anastomosis vs. Conventional End-to-End Anastomosis in the Treatment of Crohn's Disease", Dis Colon Rectum 2001; 44: No. 1, 20-26.
No author listed. Novel antibiotic coating shows potential for use on surgical implants. Healio website. Dec. 21, 2005. healio.com/orthopedics/news/online/%7Bdc0e6031-1f10-4b3c-abf6-f50b9cfd683f%7D/novel-antibiotic-coating-shows-potential-for-use-on-surgical-implants. Accessed Jun. 2, 2019. (Year: 2005).
Notice of Allowance received for U.S. Appl. No. 14/257,776, dated Mar. 25, 2016.
Oxford Dictionaries (on-line) definition of Adsorb ([Retrieved from internet <URL: http://www.oxforddictionaries.com/us/definition/american_english/adsorb >] [Downloaded Mar. 10, 2015]).
Rausch, Virtual Textbook of Organic Chemistry, Heterocyclic Chemistry, 1999, pp. 1-14, recovered from https://www2.chemistry.msu.edu/faculty/reusch /VirtTxtJml/heterocy.htm on Jun. 1, 2017.
Sigma-Aldrich, Poly(ethylene-co-vinyl acetate), [Retrieved from internet <URL: http://www.sigmaaldrich.com/catalog/product/aldrich/340502?lang=- en®ion=US >], [Downloaded Jul. 22, 2016], excerpt in action.
U.S. Appl. filed Apr. 22, 2016, Savage et al., U.S. Appl. No. 15/135,900.
U.S. Appl. filed Apr. 22, 2016, Savage et al., U.S. Appl. No. 15/135,928.
U.S. Appl. filed Apr. 22, 2016, Savage et al., U.S. Appl. No. 15/135,969.
U.S. Appl. filed Apr. 23, 2015, Beus et al., U.S. Appl. No. 14/694,028.
U.S. Appl. filed Apr. 7, 2017, Savage., U.S. Appl. No. 15/481,184.
U.S. Appl. filed Apr. 7, 2017, Savage., U.S. Appl. No. 15/481,884.
U.S. Appl. filed Aug. 19, 2015, Savage., U.S. Appl. No. 14/830,356.
U.S. Appl. filed Jan. 16, 2017, Savage., U.S. Appl. No. 15/406,667.
U.S. Appl. filed Jan. 21, 2015, Savage., U.S. Appl. No. 14/602,071.
U.S. Appl. filed Jan. 22, 2015, Savage., U.S. Appl. No. 14/602,499.
U.S. Appl. filed Jul. 25, 2014, Savage, et al., U.S. Appl. No. 14/341,304.
U.S. Appl. filed Jun. 25, 2015, Genberg et al., U.S. Appl. No. 14/750,928.
U.S. Appl. filed Mar. 11, 2015, Beus et al., U.S. Appl. No. 14/644,946.
U.S. Appl. filed Mar. 11, 2015, Savage et al., U.S. Appl. No. 14/645,040.
U.S. Appl. filed Mar. 20, 2018, Savage., U.S. Appl. No. 15/926,534.
U.S. Appl. filed Mar. 21, 2016, Beus et al., U.S. Appl. No. 15/076,313.
U.S. Appl. filed Mar. 23, 2018, Savage, Paul B., U.S. Appl. No. 15/934,534.
U.S. Appl. filed Mar. 9, 2017, Savage et al., U.S. Appl. No. 15/454,135.
U.S. Appl. filed May 3, 2017, Savage et al., U.S. Appl. No. 15/585,632.
U.S. Appl. filed Oct. 16, 2014, Savage, et al., U.S. Appl. No. 14/515,858.
U.S. Appl. filed Oct. 30, 2014, Savage, et al., U.S. Appl. No. 14/398,094.
U.S. Appl. filed Oct. 6, 2015, Savage., U.S. Appl. No. 14/875,953.
U.S. Appl. filed Sep. 1, 2015, Genberg et al., U.S. Appl. No. 14/842,582.
U.S. Appl. filed Sep. 20, 2016, Genberg et al., U.S. Appl. No. 15/270,876.
U.S. Appl. filed Sep. 25, 2015, Savage., U.S. Appl. No. 14/866,213.
U.S. Appl. filed Sep. 9, 2015, Genberg et al., U.S. Appl. No. 14/848,819.
U.S. Appl. No. 13/841,549, filed Mar. 15, 2013, Office Action dated Apr. 23, 2015.
U.S. Appl. No. 14/288,126, filed May 27, 2014, Savage et al.
U.S. Appl. No. 14/926,738, filed Oct. 29, 2015, Vazquez et al.
U.S. Appl. No. 16/184,211, filed Nov. 8, 2018, Savage.
U.S. Application filed Feb. 17, 2015, by Savage, U.S. Appl. No. 14/624,200.
U.S. Application filed Mar. 10, 2015, by Darien et al., U.S. Appl. No. 14/642,905.
U.S. Application filed Jul. 29, 2014, by Vazquez et al., U.S. Appl. No. 14/364,283.
U.S. Application filed Oct. 1, 2015, by Savage et al., U.S. Appl. No. 14/873,013.
U.S. Application filed Oct. 25, 2016, by Vazquez et al., U.S. Appl. No. 15/333,514.
U.S. Patent Application filed Jul. 23, 2014 2014 by Vazquez et al., U.S. Appl. No. 14/339,342.
U.S. Patent Application filed Mar. 20, 2020, by Savage, U.S. Appl. No. 15/926,534.
US. Appl. filed Mar. 1, 2013, Savage., U.S. Appl. No. 13/783,007.
Van Bambeke et al: "The bacterial envelope as a target for novel anti-MRSA antibiotics", Trends in Pharmacological Sciences, Elsevier, Hayworth, GB, vol. 29, No. 3, Feb. 11, 2008, pp. 124-134.
Zaragoza Dorwald, Side Reactions in Organic Synthesis, 2005, Wiley-VCH Verlag GmbH & Co. KGaA, Weinheim, Preface. p. IX.
BASF, [Retrieved from internet <URL:https://worldaccount.basf.com/wa/NAFTA.about.en_US/Catalog/ChemicalsNAFTA-/doc4/BASF/PRD/30085231/.pdf?asset_type=pi/pdf&language=EN&urn=um:documen-tum:eCommerce_sol_EU:09007bb280022b53.pdf>] (Year: 2004).
csabiotech.com, Uncategorized: CSA Biotecfinologies LLC. posted by admin on Apr. 5, 2011 (Year: 2011).
Sigma-Aldrich, Poly(ethylene-co-vinyl acetate), [Retrieved from internet <URL:http://www.sigmaaldrich.com/catalog/product/aldrich/3405027lang—en (Registered) ion=US >], [Downloaded Jul. 22, 2016], excerpt in action.
Examiner Interview Summary received for U.S. Appl. No. 14/208,082, dated Oct. 23, 2020, 4 pages.
Final Office Action received for U.S. Appl. No. 14/208,082, dated Oct. 16, 2020, 17 pages.
Final Office Action received for U.S. Appl. No. 14/341,304, dated Oct. 16, 2020, 18 pages.
Final Office Action received for U.S. Appl. No. 14/515,858, dated Oct. 23, 2020, 26 pages.

(56) References Cited

OTHER PUBLICATIONS

Non-Final Office Action received for U.S. Appl. No. 15/926,577, dated Sep. 28, 2020, 14 pages.
Non-Final Office Action received for U.S. Appl. No. 16/184,211, dated Sep. 21, 2020, 16 pages.

* cited by examiner

CSA-37

CSA-41

CSA-42

CSA-43

CSA-44

CSA-45

CSA-47

CSA-49

CSA-50

CSA-51

CSA-105

CSA-106

CSA-107

CSA-109

CSA-110

CSA-112

CSA-113

CSA-118

CSA-119

CSA-120

CSA-121

CSA-121a

CSA-122

CSA-123

CSA-124

CSA-130

CSA-131

CSA-132

90% with CaDPA
10% without CaDPA

0% with CaDPA
100% without CaDPA

0% with CaDPA
100% without CaDPA

USE OF CATIONIC STEROIDAL ANTIMICROBIALS FOR SPORICIDAL ACTIVITY

CROSS-REFERENCE TO RELATED APPLICATIONS

This Application claims the benefit of U.S. Provisional Patent Application No. 62/474,495, filed Mar. 21, 2017, the disclosure of which is incorporated herein by reference in its entirety.

BACKGROUND

Spore-forming bacteria are a class of microorganisms with the ability to survive in extreme environmental conditions. Morphological features of spores provide resistance to stress factors such as high temperature, radiation, disinfectants, and drying. Consequently, spore elimination in industrial and medical environments is very challenging.

Spore-forming bacteria, such as *Bacillus* and *Clostridium* species, are able to produce spores in response to environmental conditions such as limited nutrients. Spore formation results in the generation of metabolically dormant and environmentally resistant cells with enhanced ability to survive high temperature, UV and gamma radiation, antibiotic treatment, and extreme environmental conditions. Spore-forming bacteria frequently occur in food products, and they are responsible for food spoilage and food-borne diseases. Importantly, dormant spores of some bacteria, such as *Clostridium* species, are an infectious and transmissible form of the microbe. In another example, the persistence of spores, their germination, and their outgrowth into the vegetative form is responsible for a re-emergence of *Clostridium difficile* infections, even after long-term antibiotic treatment.

Bacterial spores formed in sporulation processes are extremely resistant to physical sterilization processes, antibiotics, and other antimicrobial agents. The structure of a spore plays a crucial role in the protection of cells against stressful environmental conditions. The spore coat aids in the resistance of spores against some chemicals and lytic enzymes and increases resistance of cells to heat, radiation, or a variety of select chemical decontaminates. The inner membrane of spores represents a strong permeability barrier, significantly defending internal structures of spores, including DNA, and playing a vital role in the development of chemical resistance. See Cortezzo, D. E. and Setlow, P., "Analysis of factors that influence the sensitivity of spores of *Bacillus subtilis* to DNA damaging chemicals," *J Appl Microbiol*, 2005. 98(3): p. 606-17. Thus, agents with the ability to by-pass permeability barriers of spores can potentially provide sporicidal activity.

Other factors providing resistance to bacterial spores include lower water content and high mineralization of spore cores, high levels of dipicolinic acid (DPA) and its associated divalent cations (mostly CaDPA), the protection of spore DNA against wet heat damage by its saturation with α/β-type small, acid-soluble proteins (SASPs), the presence of UV-absorbing pigments located in the spore's outer layers and DNA damage repair mechanisms during spore germination and outgrowth.

Most research on sporicidal agents has focused on the application of reactive chemical compounds, many of which are toxic to humans and therefore have limited application. Oxidizing agents and acid solutions may induce alterations in the spore membranes sufficient to kill the spores or considerably affect their ability to germinate and grow in typical environmental conditions.

It was reported that peroxynitrite and acids appear to kill spores by damaging the spore's external layers, including the inner membrane, resulting in spore death. See Genest, P. C., et al., "Killing of spores of *Bacillus subtilis* by peroxynitrite appears to be caused by membrane damage," *Microbiology*, 2002. 148(Pt 1): p. 307-14. Treatment of spores with hydrogen peroxide causes dysfunction of spore germination. See Melly, E., Cowan, A. E., and Setlow, P., "Studies on the mechanism of killing of *Bacillus subtilis* spores by hydrogen peroxide," *J Appl Microbiol*, 2002. 93(2): p. 316-25. However, there are many applications for which these harsh agents cannot suitably be used. Additionally, enzymes present in the spore coat, including superoxide dismutase, might detoxify some of such oxidizing agents before they penetrate into the deeper parts of the spore, which can significantly reduce their usefulness. See Henriques, A. O., Melsen, L. R., and Moran, C. P., "Involvement of superoxide dismutase in spore coat assembly in *Bacillus subtilis*," *J Bacteriol*, 1998. 180(9): p. 2285-91.

BRIEF SUMMARY

The disclosure relates generally to sporicidal compositions which include one or more cationic steroidal antimicrobial (CSA) compounds, and methods of killing or deactivating spores using such compositions.

Some embodiments are directed to methods of killing or deactivating bacterial spores on one or more objects to which a sporicidal composition is applied. In some embodiments, a method includes (1) applying a sporicidal composition having one or more CSA compounds to an object that has or may have bacterial spores, and (2) the sporicidal composition killing or deactivating one or more bacterial spores contacting the sporicidal composition. The object treated can be surfaces, spaces, or regions of confined air of a building, hospital, air duct, restaurant, food preparation facility, school, office, or a medical device.

At least some of the sporicidal compositions disclosed herein are safe and non-toxic to humans and animals. In particular, the one or more CSA compounds included the disclosed sporicidal compositions are safe and non-toxic relative to the harsh sporicidal agents typically utilized to kill bacterial spores, including agents such as acids and oxidizers. Certain sporicidal compositions described herein may therefore be provided in a non-acidic form and/or in a form that does not rely on oxidation to kill or deactivate bacterial spores. Certain sporicidal compositions described herein may be applied to or mixed with a food product to reduce spoilage of the food product and/or to reduce the occurrence of food borne illness associated with bacterial spores.

Some embodiments are directed to methods of therapeutically or prophylactically treating or preventing an infection associated with spore-forming bacteria. In some embodiments, a method includes (1) administering a composition having one or more CSA compounds to a subject having or at risk of contracting a spore-forming bacterial infection, and (2) the sporicidal composition killing or deactivating one or more bacterial spores coming into contact with the sporicidal composition, thereby therapeutically or prophylactically treating the subject.

BRIEF DESCRIPTION OF DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Overview of CSA Compounds

Cationic sterioidal antibiotic ("CSA") compounds ("CSAs"), which are also known as "ceragenin" compounds (or "ceragenins"), are synthetically produced small molecule chemical compounds that include a sterol backbone having various charged groups (e.g., amine, guanidine, and/or other groups capable of exhibiting cationic properties under biological conditions) attached to the backbone. The backbone can be used to orient the cationic groups on one face, or plane, of the sterol backbone. In general, the term "CSA compound" refers to the type or structure of the CSA, while the term "CSA molecule" refers to the CSAs themselves when used in a sporicidal composition.

CSAs are cationic and amphiphilic, based upon the functional groups attached to the backbone. They are facially amphiphilic with a hydrophobic face and a polycationic face. Without wishing to be bound to any particular theory, it is theorized that the CSA compounds described herein act as effective sporicidal agents by interacting with and disrupting the multilayered structure of the spores, bypassing the relative impermeability of the spore's inner membrane, and/or damaging the DNA within the spore core. It is also theorized that the charged groups are responsible for interacting with the bacterial spores, and without the charged groups, the CSA molecules would less effectively interact with and disrupt the spores.

Figure 1:
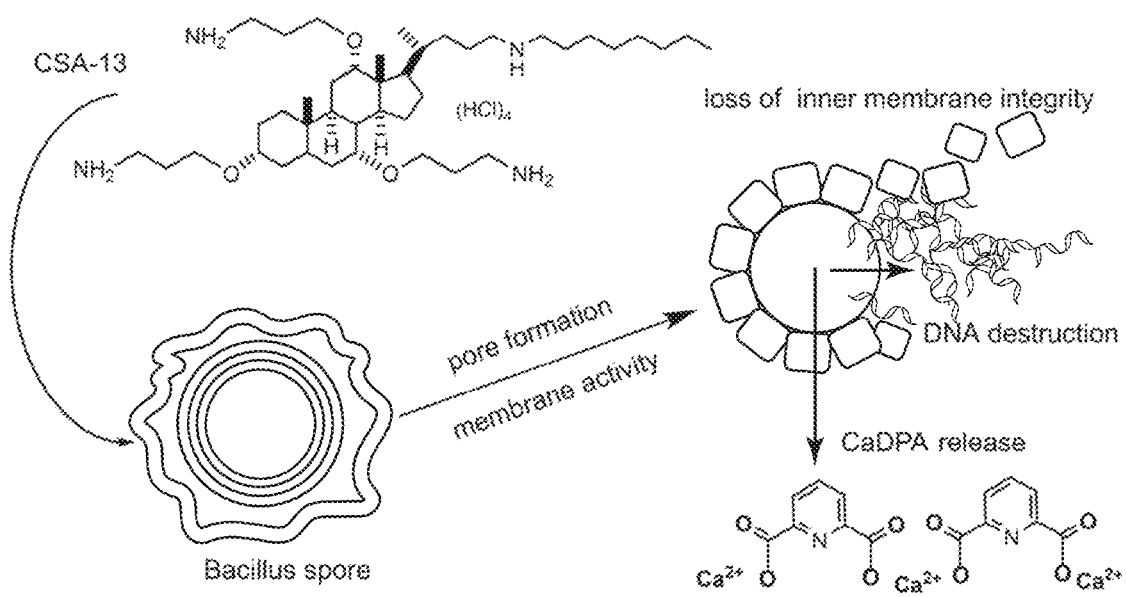
FIG. 1 illustrates a theorized mechanism of CSA sporicidal activity.

FIG. 1 illustrates a theorized mechanism for a CSA molecule's sporicidal activity. Considering that the loss of spore DPA is followed by replacement of this compound by water, it is theorized that alterations in core hydration are associated with the CSA-induced release of CaDPA from the spore core as the result of membrane-permeabilizing properties of the CSA (CSA-13 is shown as an example). The release of DPA from the spore core results from alterations in permeability of spore barriers, likely including the spore inner membrane, which allows for increased accessibility of the spore core to exogenous factors. This process involves a simultaneous increase in spore hydration. It is therefore possible that sporicidal properties of CSA compounds (which are shown to be elevated at higher temperatures) result from CaDPA release, which is followed by eradication of the DPA-depleted spores and associated increases in sensitivity of the spores.

An example of a CSA compound is shown below as Formula I. As will be discussed in greater detail below, the R groups of Formula I can have a variety of different functionalities, thus providing a given ceragenin compound with specific, different properties. In addition, as will be appreciated by those of skill in the art, the sterol backbone can be formed of 5-member and/or 6-member rings, so that p, q, m, and n may independently be 1 (providing a 6-member ring) or 0 (providing a 5-member ring).

(I)

Figure 2A:
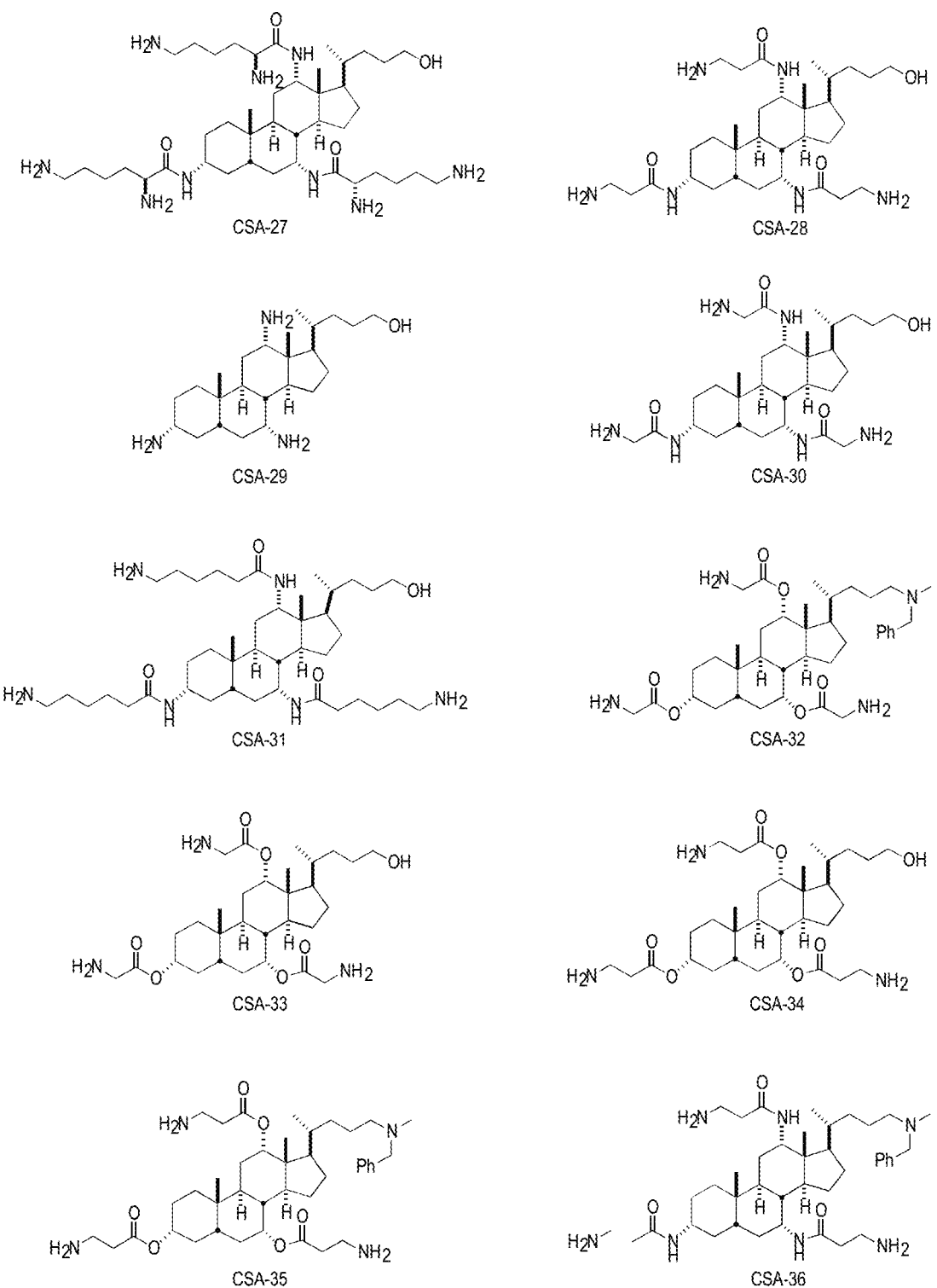
FIGS. 2A-2C illustrates examples of cationic steroidal antimicrobial compounds.
Figure 2A:
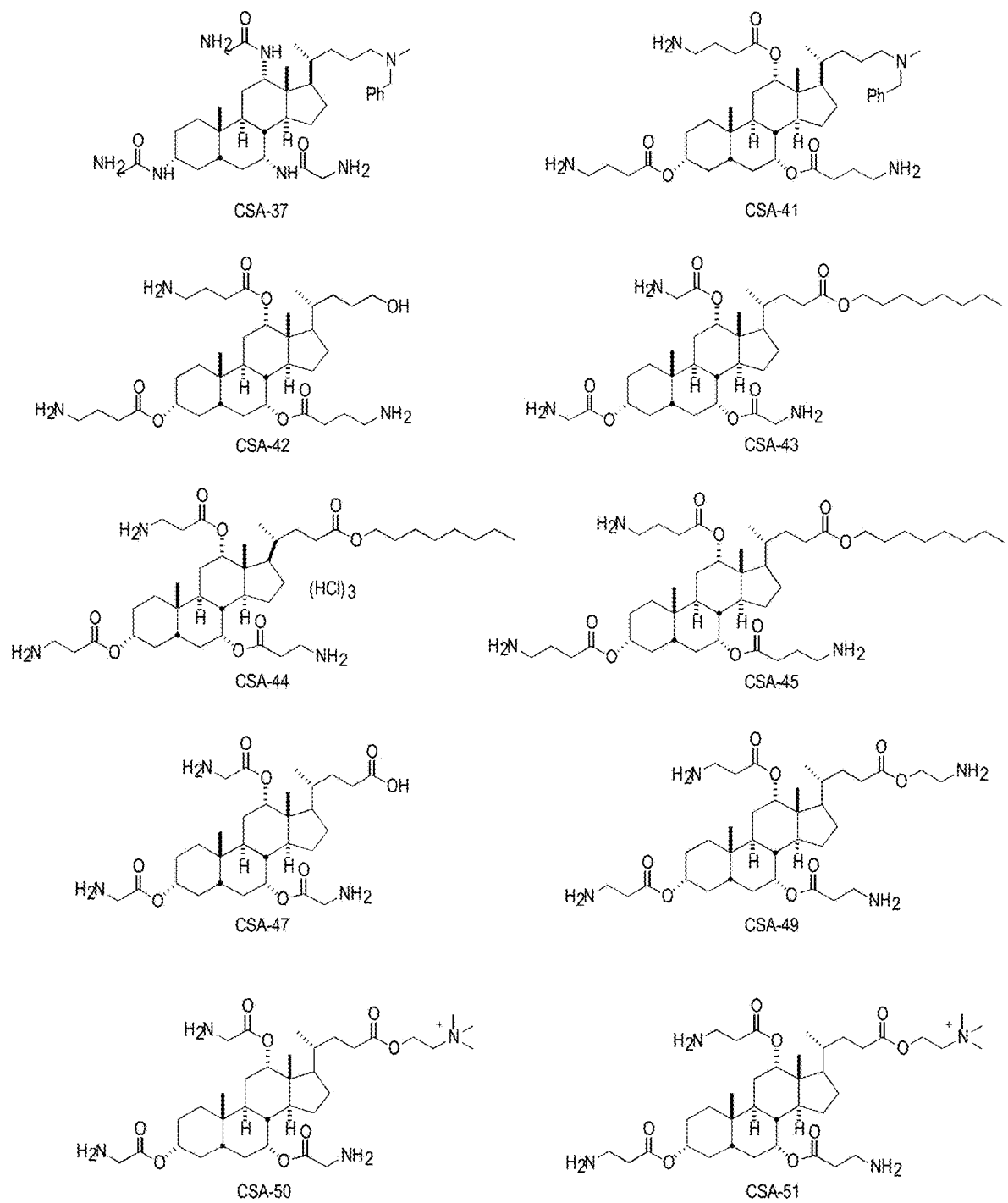
Figure 2A:
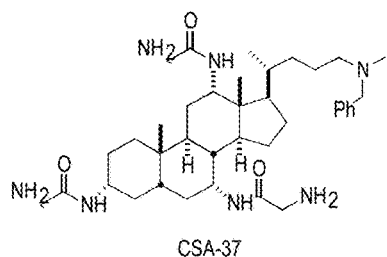
Figure 2A:
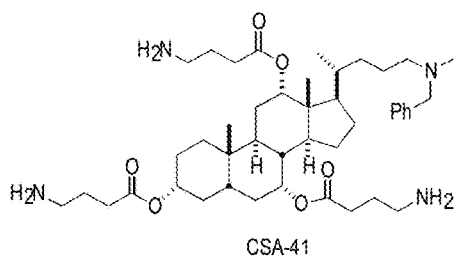
Figure 2A:
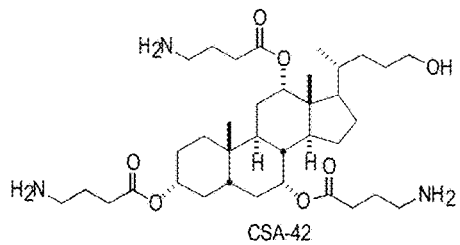
Figure 2A:
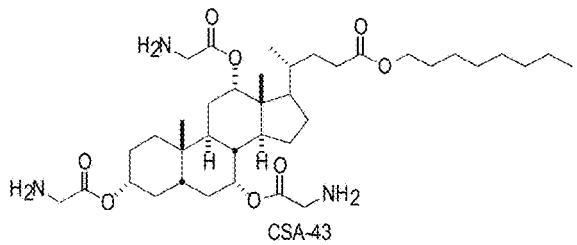
Figure 2A:
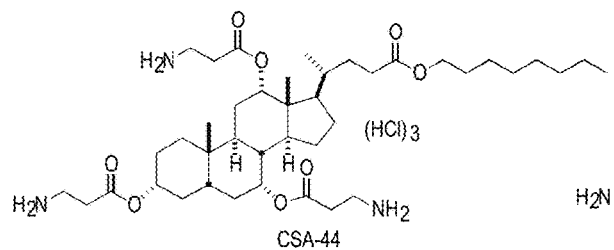
Figure 2A:
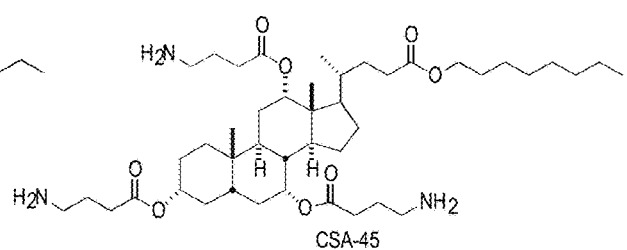
Figure 2A:
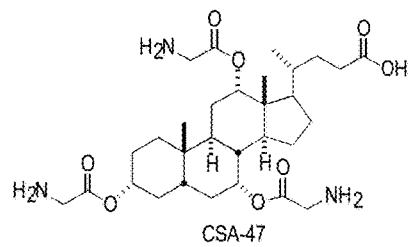
Figure 2A:
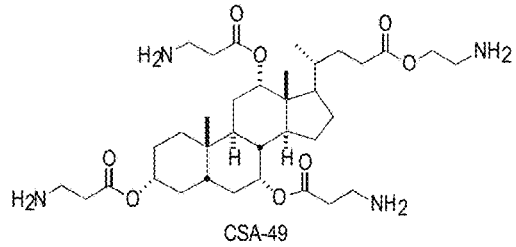
Figure 2A:
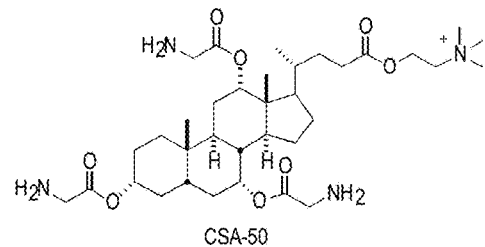
Figure 2A:
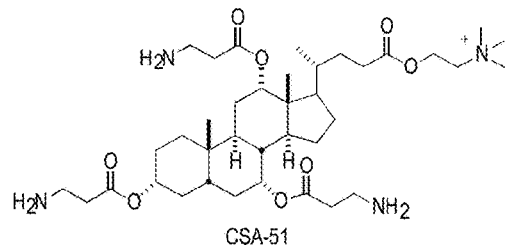
Figure 2B:
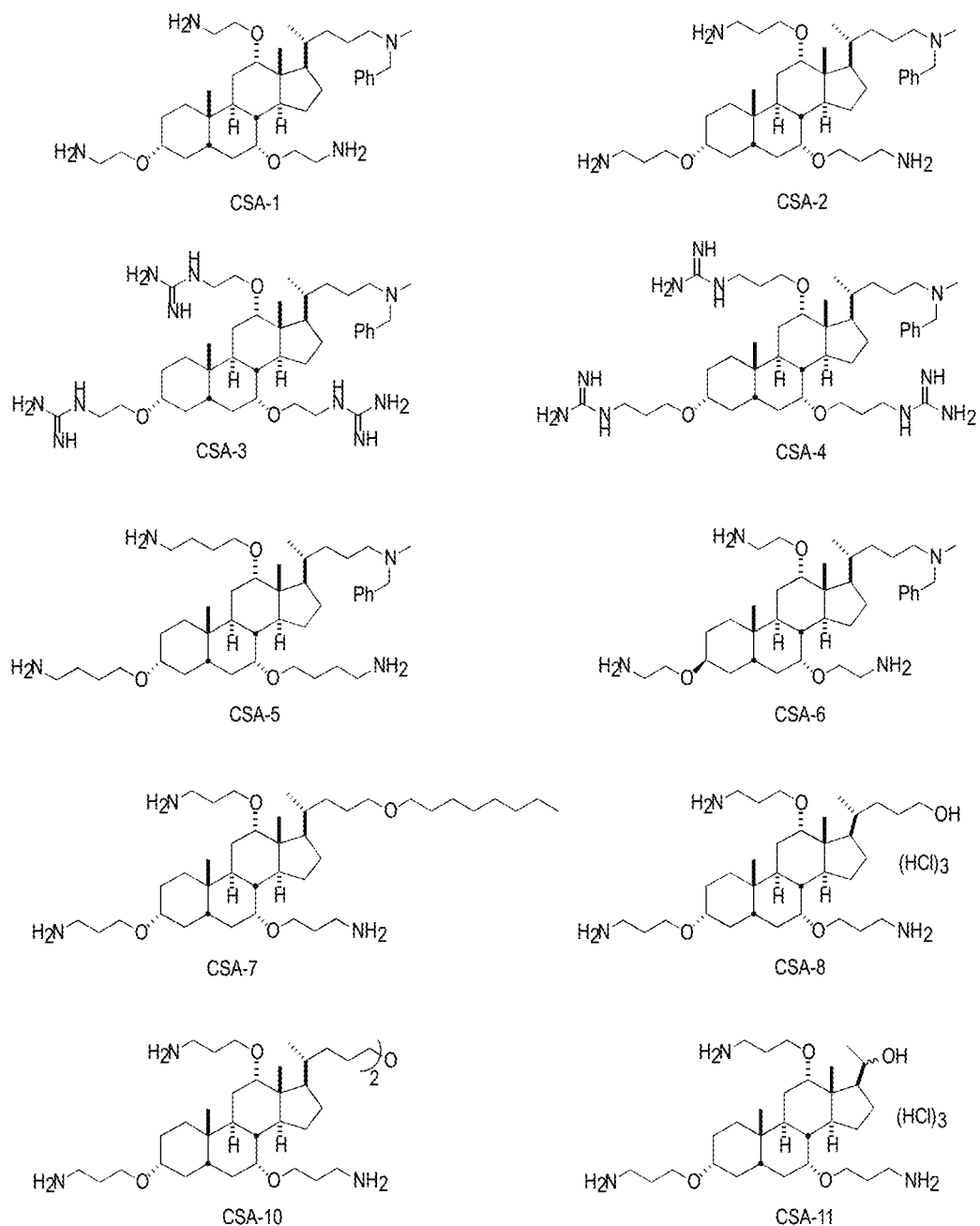
Figure 2B:
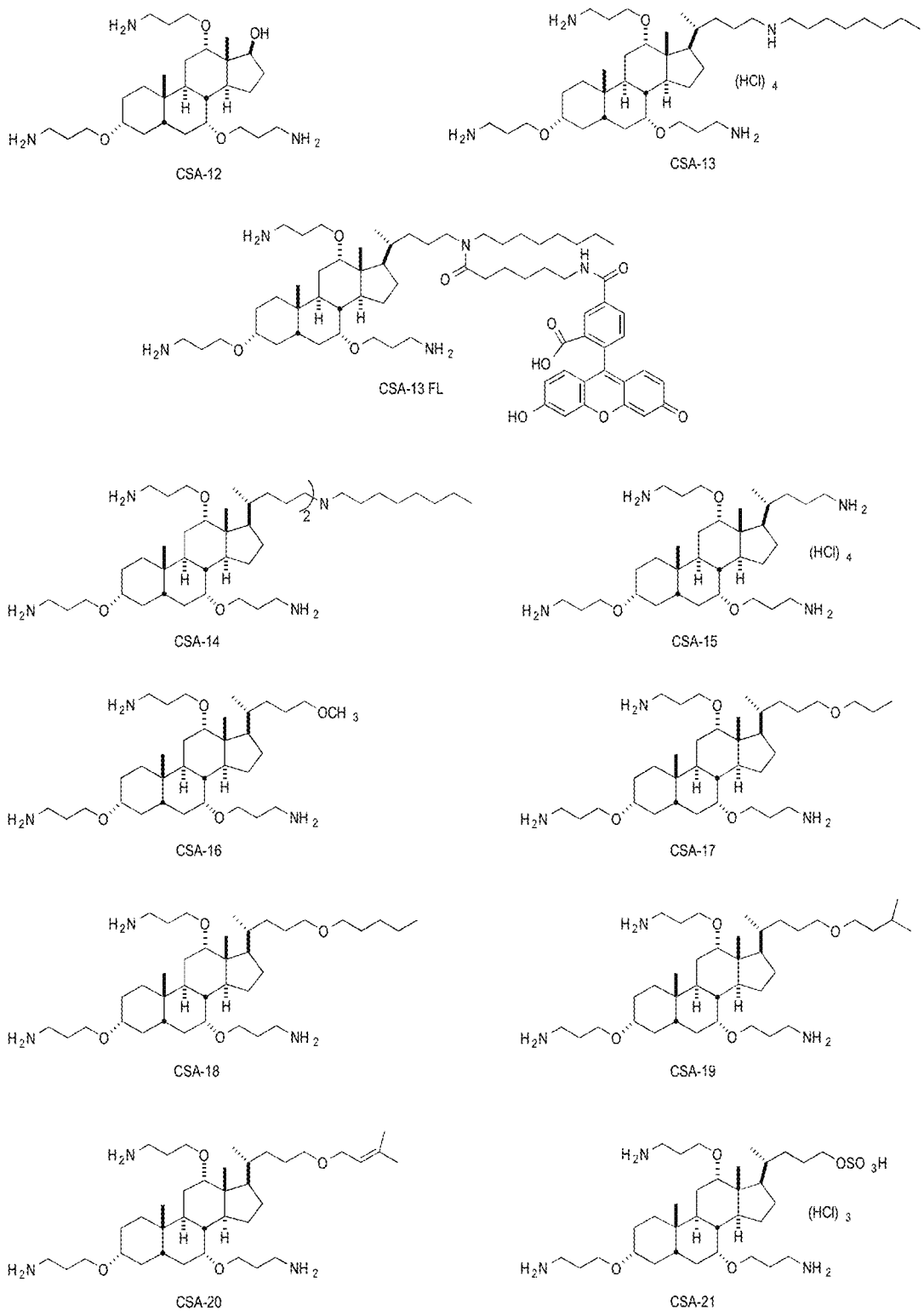
Figure 2B:
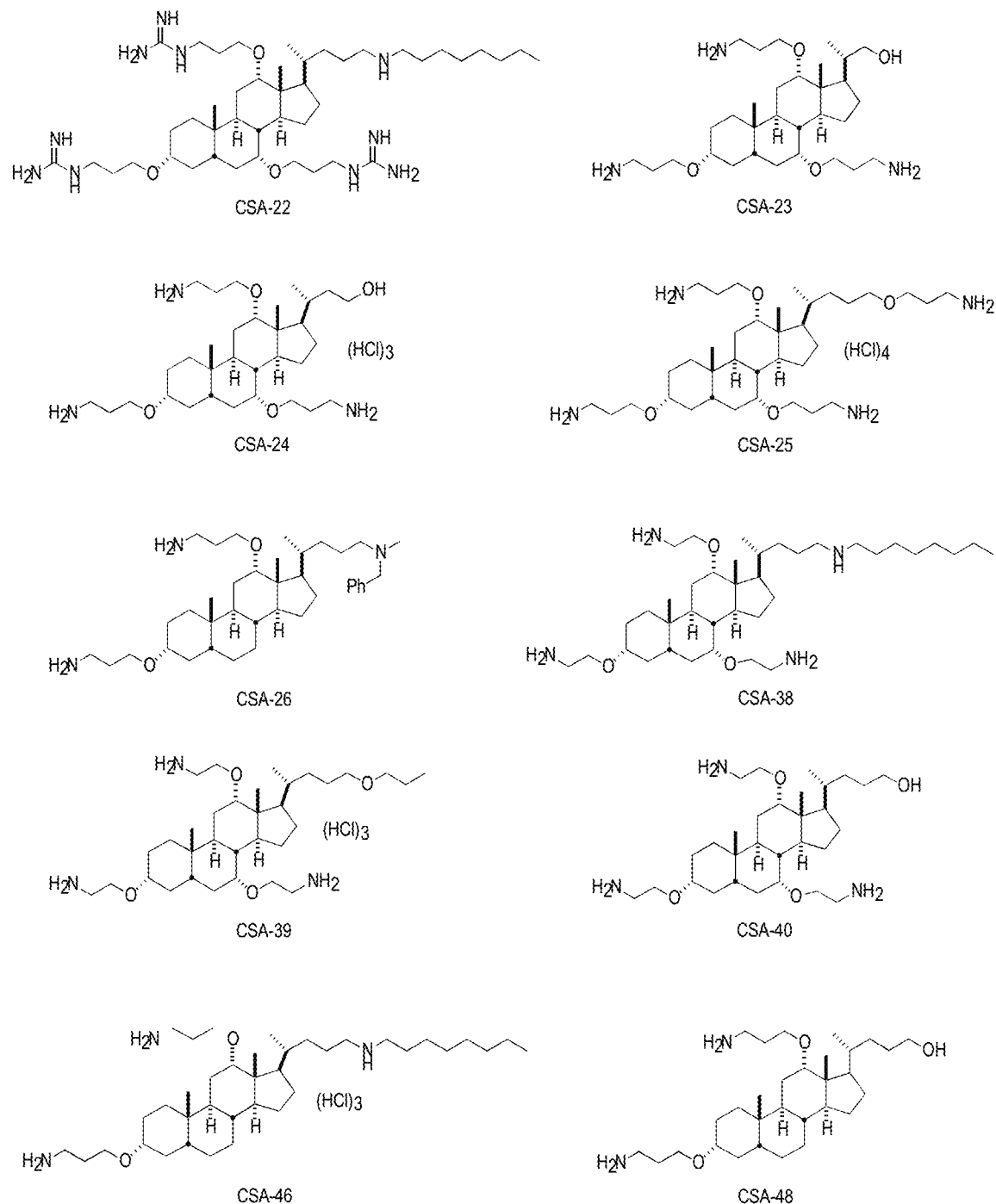
Figure 2B:
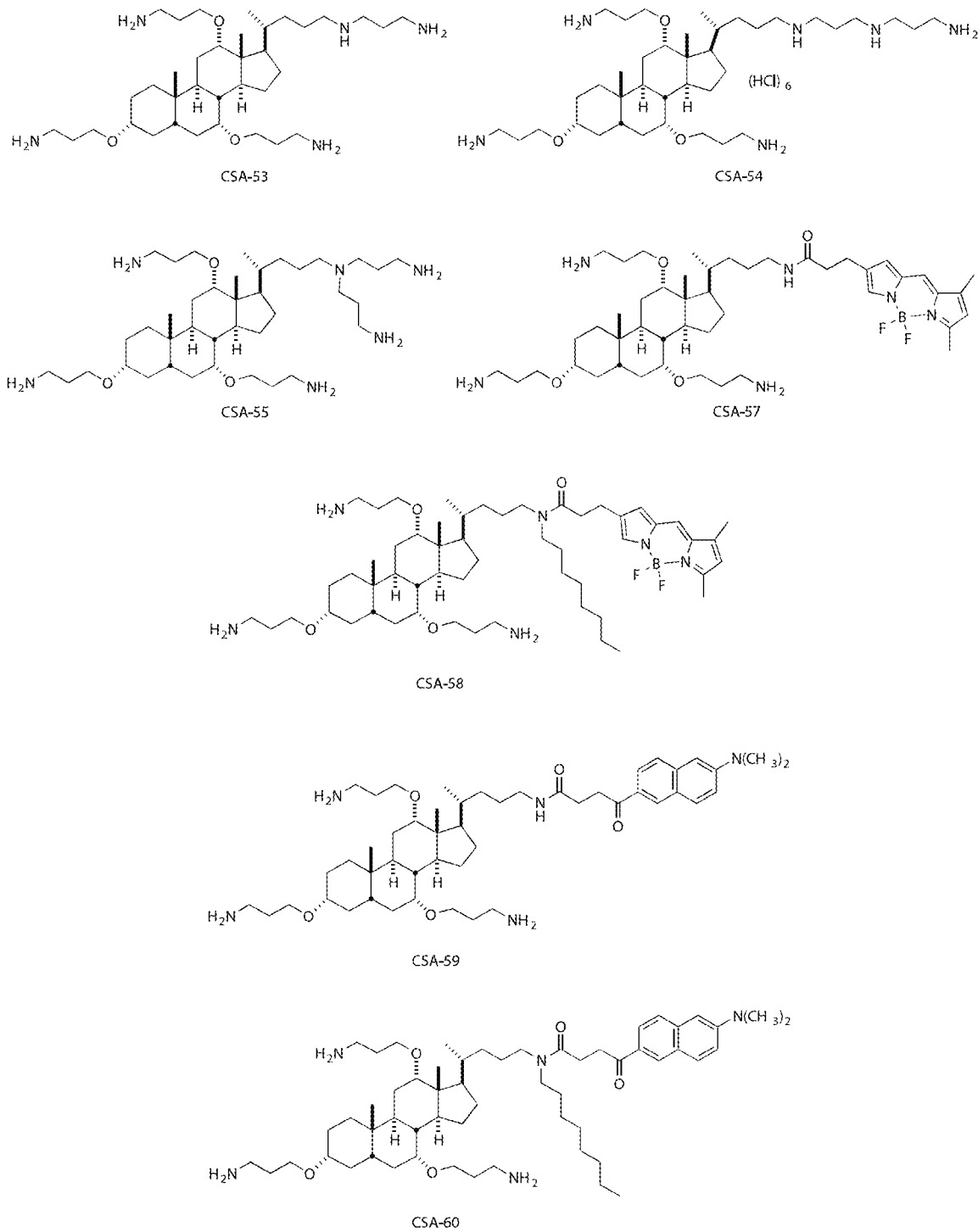
Figure 2B:
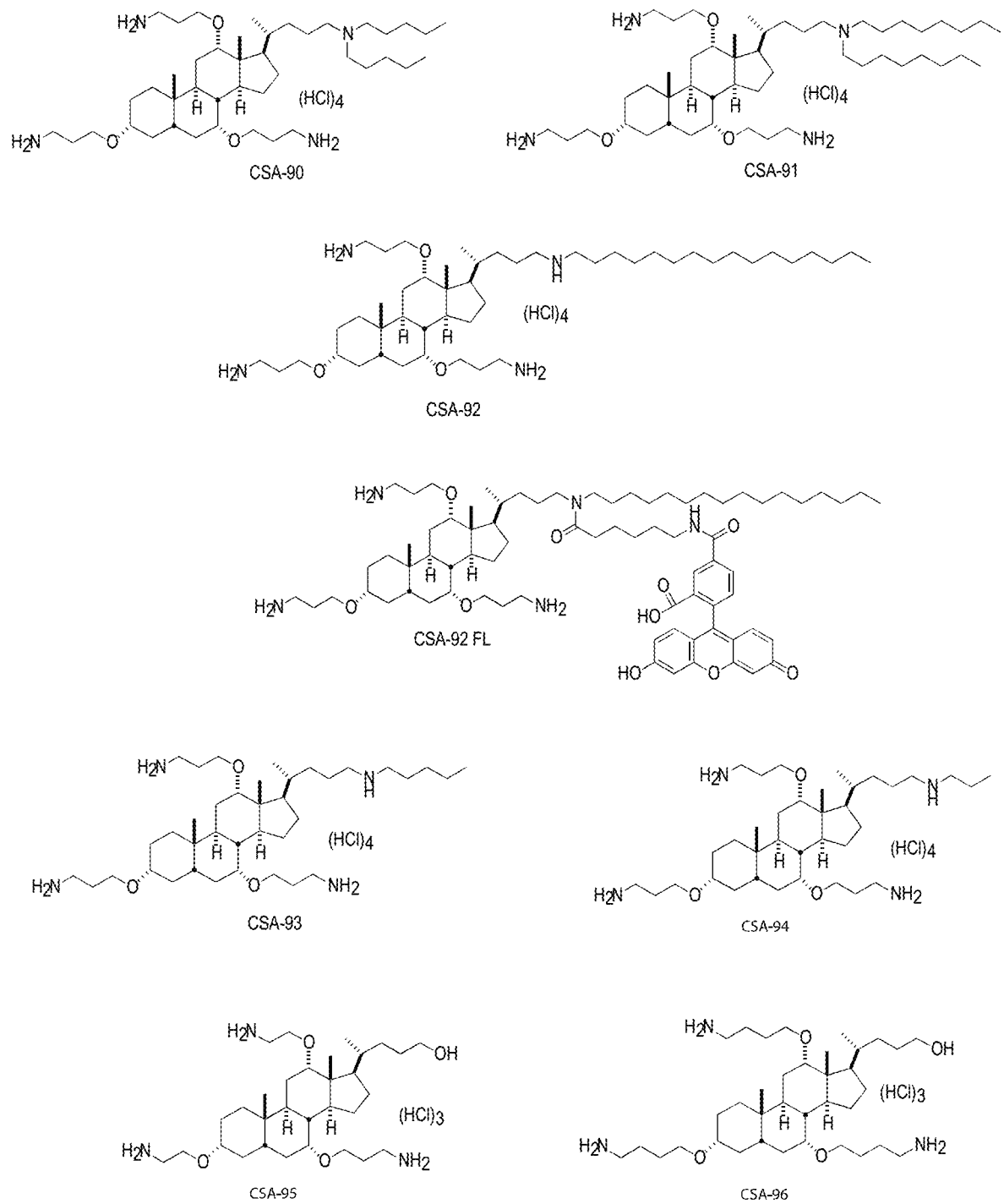
Figure 2B:
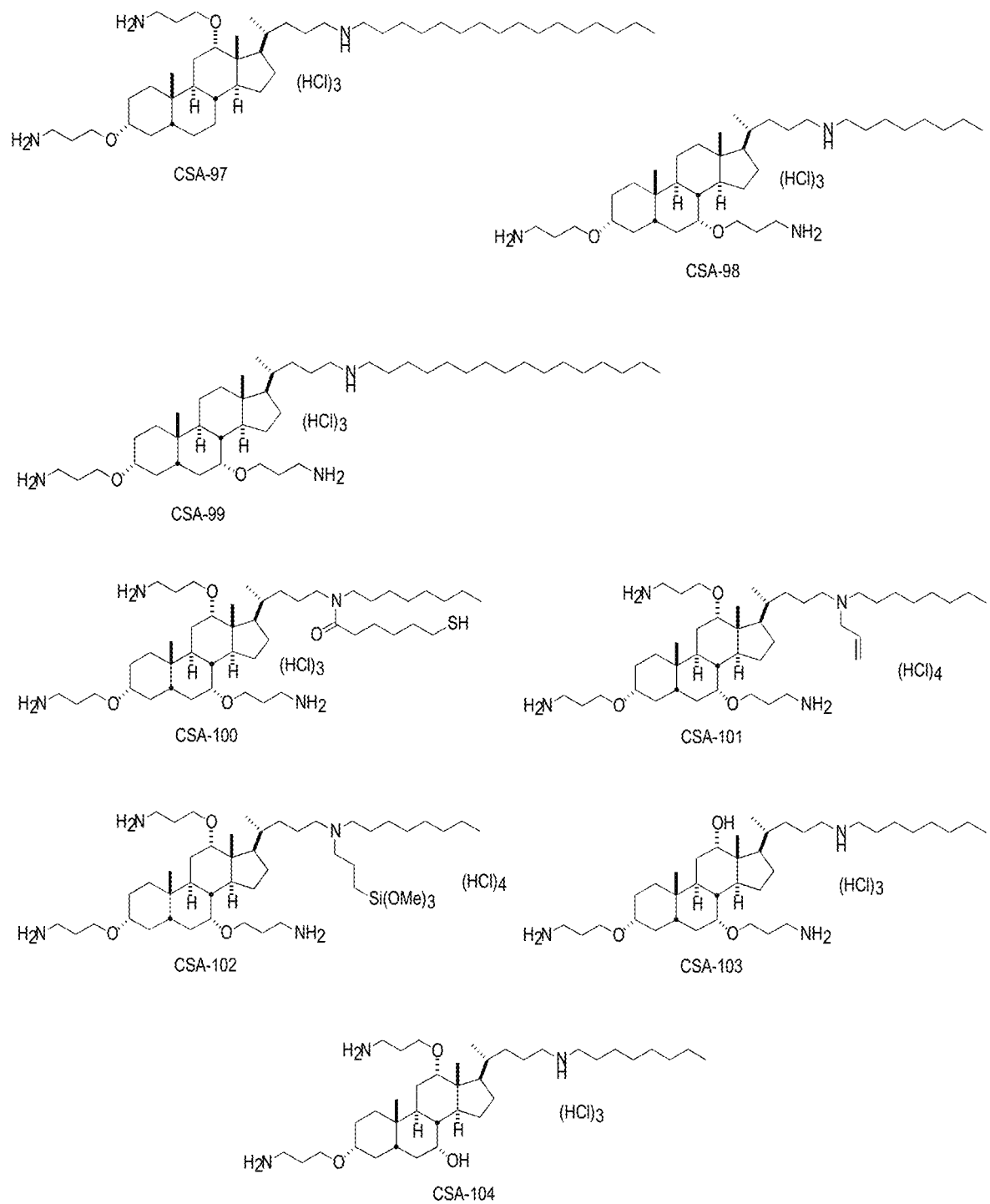
Figure 2B:
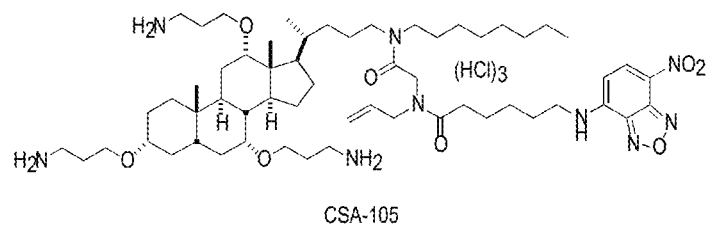
Figure 2B:
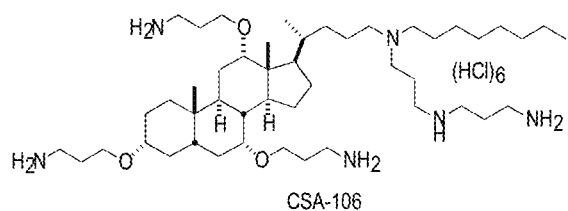
Figure 2B:
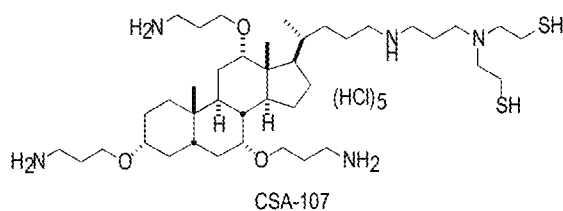
Figure 2B:
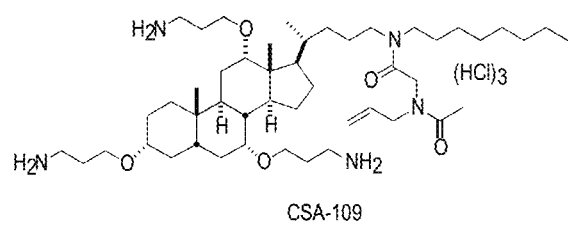
Figure 2B:
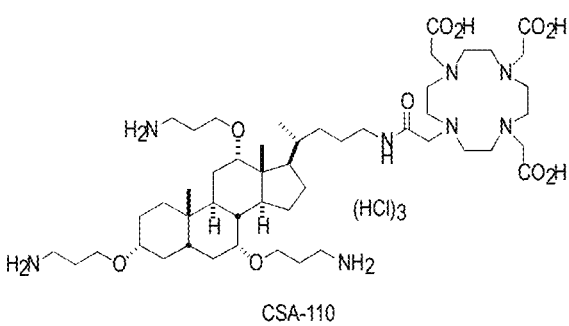
Figure 2B:
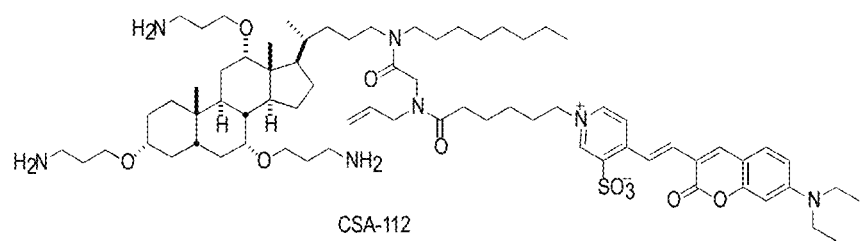
Figure 2B:
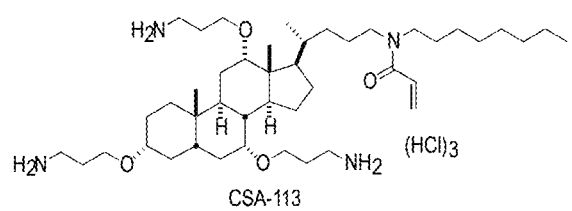
Figure 2B:
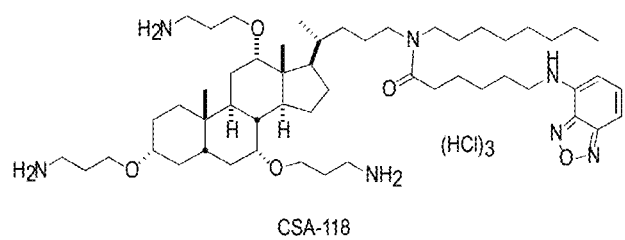
Figure 2B:
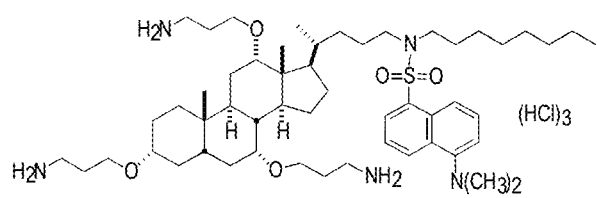
Figure 2B:
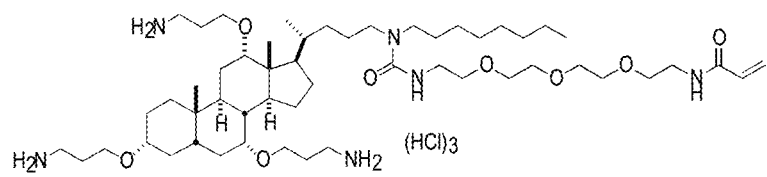
Figure 2B:
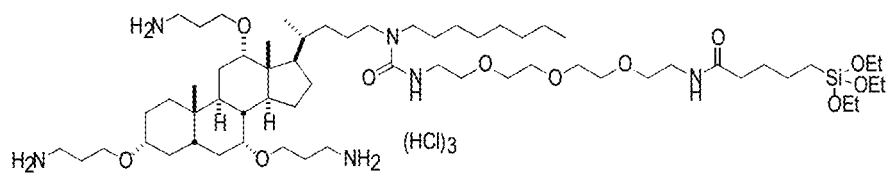
Figure 2B:
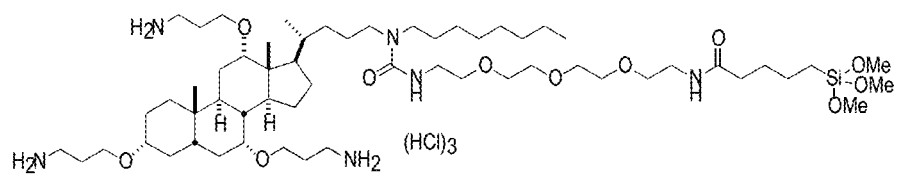
Figure 2B:
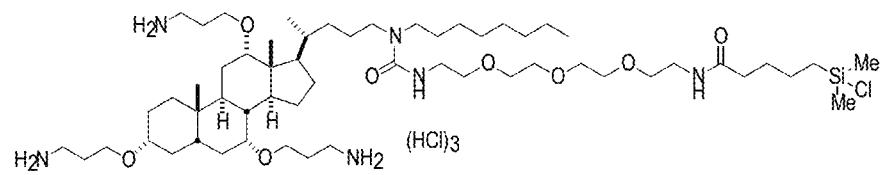
Figure 2B:
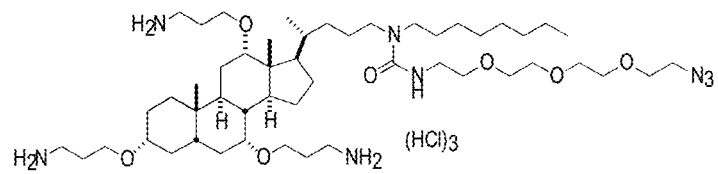
Figure 2B:
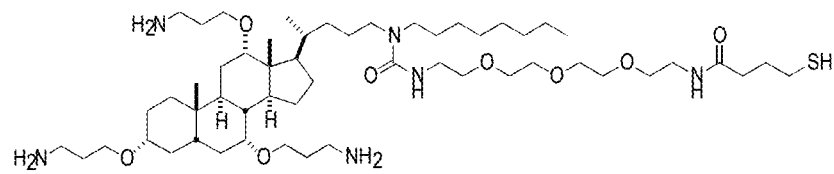
Figure 2B:
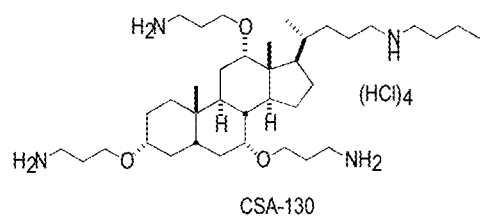
Figure 2B:
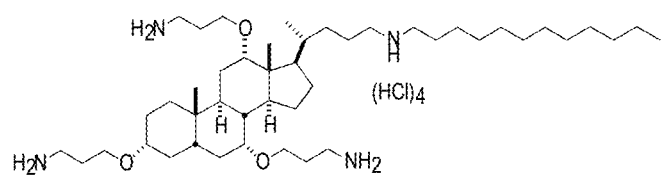
Figure 2B:
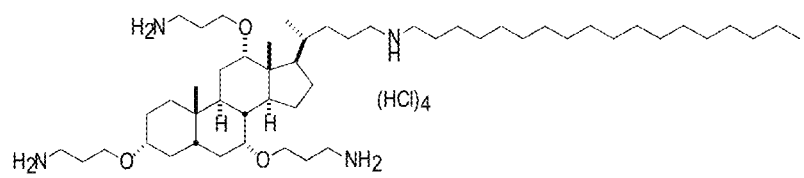
Figure 2B:
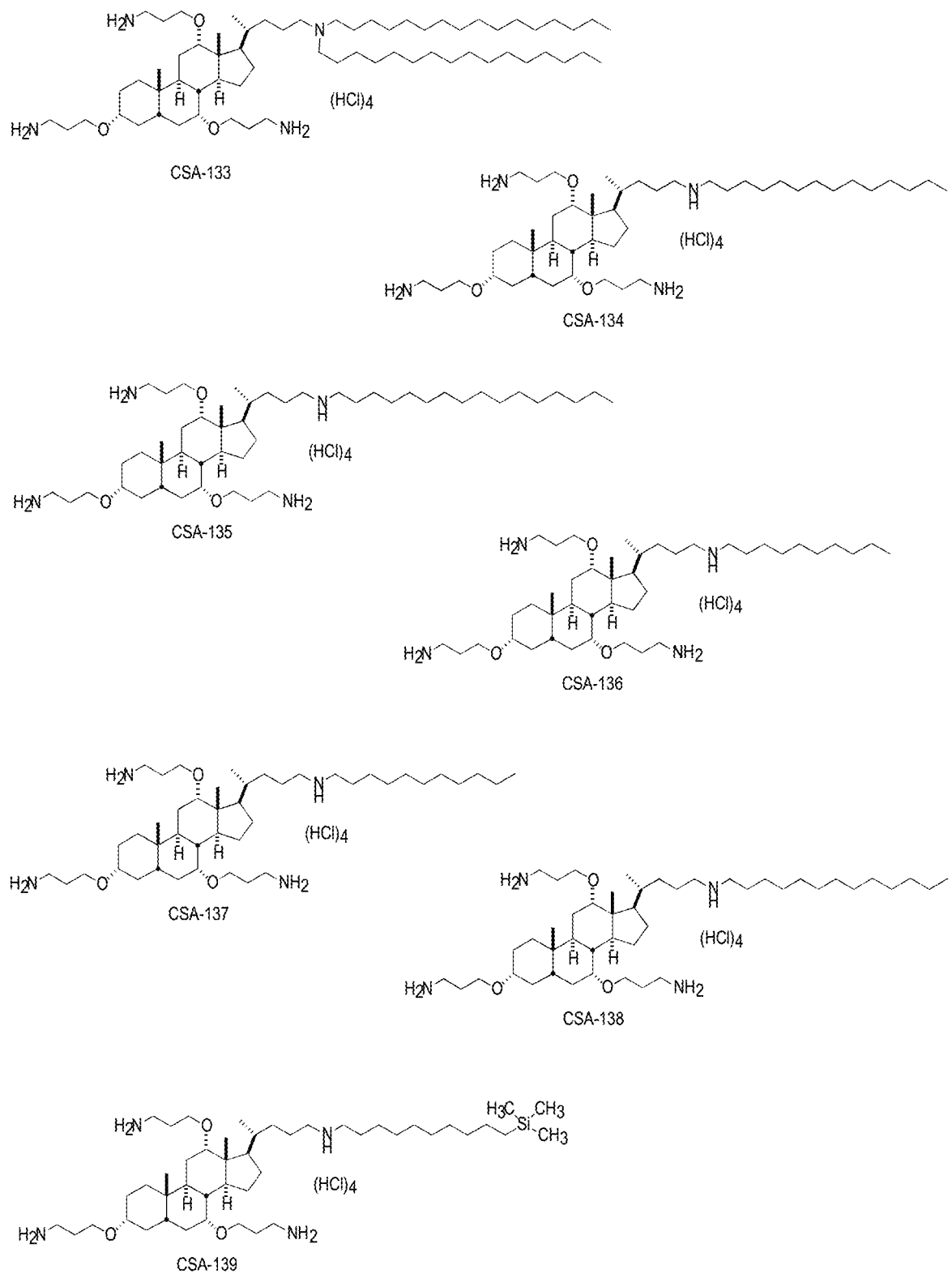
Figure 2C:
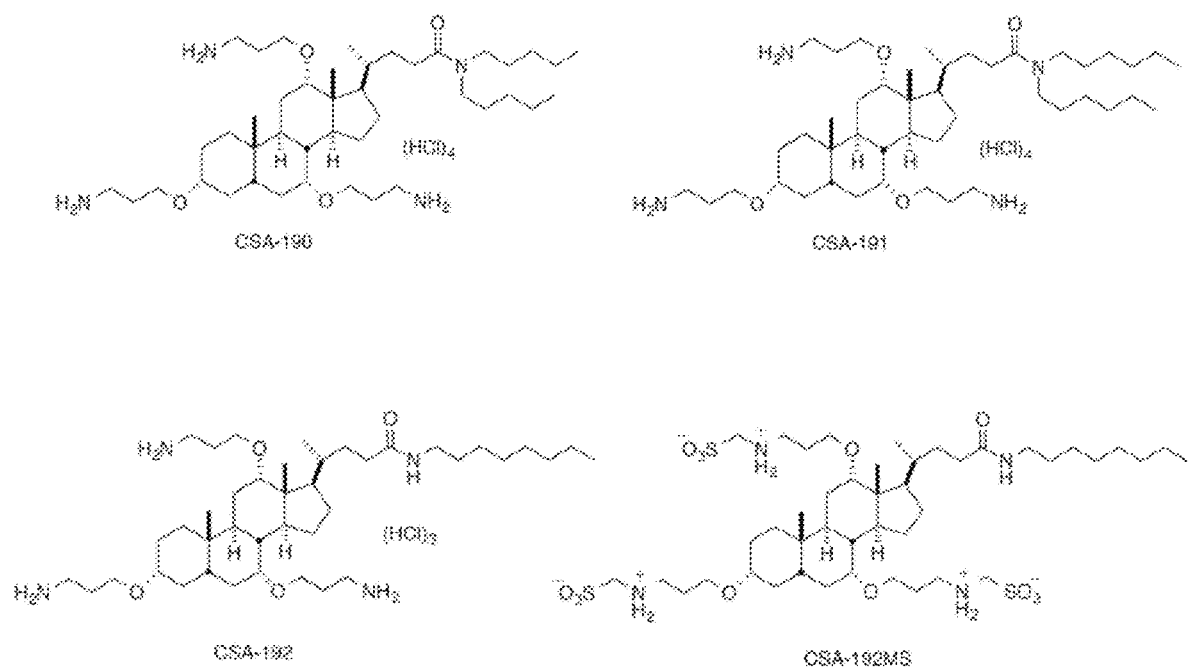

A number of examples of CSA compounds of Formula I that can be incorporated into the medical devices described herein are illustrated in FIGS. 2A-2C.

Typically, the CSAs of Formula I are of two types: (1) CSA compounds having cationic groups linked to the sterol backbone with hydrolysable linkages and (2) CSA compounds having cationic groups linked to the sterol backbone with non-hydrolysable linkages. For example, one type of hydrolysable linkage is an ester linkage, and one type of non-hydrolysable linkage is an ether linkage. CSA compounds of the first type can be "inactivated" by hydrolysis of the linkages coupling the cationic groups to the sterol backbone, whereas CSA compounds of the second type are more resistant to degradation and inactivation.

In some applications, it may be desirable for a sporicidal composition to maintain sporicidal effects for as long as possible. In other applications, the spreading of CSA molecules beyond the application site may be a concern. Some embodiments can be formed using an appropriate mixture of CSAs having hydrolysable and non-hydrolysable linkages to provide desired duration of CSA activity once the CSAs are exposed to hydrolyzing conditions (e.g., once eaten by a consumer of a treated food product).

A number of examples of compounds of Formula I that may be used in the embodiments described herein are illustrated in FIGS. 2A-2C. Examples of CSA compounds with non-hydrolysable linkages include, but are not limited to, CSA-1, CSA-26, CSA-38, CSA-40, CSA-46, CSA-48, CSA-53, CSA-55, CSA-57, CSA-60, CSA-90, CSA-107, CSA-109, CSA-110, CSA-112, CSA-113, CSA-118, CSA-124, CSA-130, CSA-131, CSA-139, CSA-190, CSA-191 and CSA-192. Suitable examples of CSA compounds with hydrolysable linkages include, but are not limited to CSA-27, CSA-28, CSA-29, CSA-30, CSA-31, CSA-32, CSA-33, CSA-34, CSA-35, CSA-36, CSA-37, CSA-41, CSA-42, CSA-43, CSA-44, CSA-45, CSA-47, CSA-49, CSA-50, CSA-51, CSA-52, CSA-56, CSA-61, CSA-141, CSA-142, CSA-144, CSA-145 and CSA-146. In a presently preferred embodiment, at least a portion of the CSA compounds incorporated into the sporicidal composition are CSA-13.

In Formula I, at least two of $R_3$, $R_7$, or $R_{12}$ may independently include a cationic moiety attached to the Formula I structure via a hydrolysable (e.g., an ester) or non-hydrolizable (e.g., an ether) linkage. Optionally, a tail moiety may be attached to Formula I at $R_{18}$. The tail moiety may be charged, uncharged, polar, non-polar, hydrophobic, or amphipathic, for example, and can thereby be selected to adjust the properties of the CSA and/or to provide desired characteristics.

The sporicidal activity of the CSA molecules can be affected by the orientation of the substituent groups attached to the backbone structure. In one embodiment, the substituent groups attached to the backbone structure are oriented on a single face of the CSA molecule. Accordingly, each of $R_3$, $R_7$, and $R_{12}$ may be positioned on a single face of Formula I. In addition, $R_{18}$ may also be positioned on the same single face of Formula I.

II. Compositions and Methods Utilizing CSA Compounds

Some embodiments are directed to compositions and methods for killing or deactivating bacterial spores on one or more objects. In some embodiments, a method includes (1) applying a sporicidal composition having one or more CSA compounds to an object that has or may have bacterial spores, and (2) the sporicidal composition killing or deactivating one or more bacterial spores contacting the sporicidal composition. The object treated can be surfaces, spaces, or regions of confined air of a building, hospital, air duct, restaurant, food preparation facility, school, office, or a medical device.

At least some of the sporicidal compositions disclosed herein are safe and non-toxic to humans and animals. In particular, the one or more CSA compounds included the disclosed sporicidal compositions are safe and non-toxic relative to the harsh sporicidal agents typically utilized to kill bacterial spores, including agents such as acids and oxidizers. Certain sporicidal compositions described herein may therefore be provided in a non-acidic form and/or in a form that does not rely on oxidation to kill or deactivate bacterial spores.

Further, certain CSA-containing sporicidal compositions may beneficially be utilized to treat food products with relatively minimal chemical disruption of the food product (e.g., without oxidizing the food product and/or without causing proton donation to the food product molecules). In some embodiments, the sporicidal composition is non-oxidizing. In some embodiments, the sporicidal composition has a pH of between about 6 and 8, or between about 6.5 and 7.5, or a pH of about 7.

In some embodiments, a sporicidal composition is utilized to prophylactically treat, prevent, or reduce infection(s) that may result from contact with a bacterial spore. For example, the sporicidal composition may be utilized in a healthcare facility (such as a doctor's office, hospital, nursing home, etc.) to sanitize surfaces, bedding, clothing, medical devices (e.g., colonoscopes, catheters, feeding tubes, I-V lines, medical implants, specula, dental tools, and the like) and/or other objects by killing or deactivating bacterial spores which may be present. Such a sporicidal composition can function to prevent transmission of bacterial spores from a contaminated object or surface to an individual, thereby preventing or reducing the occurrence of spore-related bacterial infections.

In some embodiments, a sporicidal composition is utilized to reduce, prevent, or eliminate food spoilage resulting from contamination of food with bacterial spores. For example, the sporicidal composition may be applied to and/or mixed within a food product to extend the shelf life of the food product. Such a sporicidal composition can function to prevent or reduce the occurrence of bacterial spores germinating at or within the food product and spoiling the food product. A sporicidal composition may be applied to and/or mixed with any suitable food product, including produce, bread, cereal, meat, dairy products, processed foods, liquid foods (juice, milk), and the like.

In certain embodiments, a CSA-containing sporicidal composition is utilized to prevent or reduce food-borne illness(es). When applied to and/or mixed with a food product, the sporicidal composition may kill or deactivate spores associated with a food-borne illness. For example, the sporicidal composition may be utilized to kill or deactivate spores associated with *C. botulinum, C. perfringens, B. cereus, B. subtilis, B. licheniformis*, and other spores capable of causing a food-borne illness.

By way of further example, a CSA-containing sporicidal composition may be used to treat drinking water. Killing and/or deactivating spores within drinking water can beneficially prevent or reduce pathological and public health effects associated with spore-contaminated drinking water.

In certain embodiments, a CSA-containing sporicidal composition is utilized to treat a subject (e.g., a human or animal) for one or more diseases associated with spore-forming bacteria. For example, a sporicidal composition may be administered to a subject suffering from or at risk of suffering from a *C. difficile* infection. It will be understood that such treatment may be done as part of treating a diagnosed disease, or as part of a prophylactic regimen intended to prophylactically treat (or prevent) occurrence of the disease. *C. difficile* infections often arise as a result of antibiotic treatment, which often eliminates bacterial competition in the intestines and allows *C. difficile* spores to germinate and outgrow relatively unchecked. In one example, therefore, a CSA-containing sporicidal composition may be combined with typical antibiotics or may be administered in conjunction with typical antibiotics to reduce the risk of a resulting spore associated infection.

In embodiments in which a sporicidal composition is administered to a subject to therapeutically or prophylactically treat or prevent an infection associated with spore-forming bacteria, the sporicidal composition may include a pharmaceutically acceptable carrier, such as a solvent, saline solution, emulsion, suspension, syrup, excipient, dispersion and suspension media, lubricant, stabilizer, thickening agent, tablet, capsule, microbead, powder, granule, crystal, and/or viscosity enhancer. The sporicidal composition may be administered according to particular treatment needs. For example, the sporicidal composition may be administered orally, rectally, intravenously, topically, nasally, parenterally, and/or through other suitable administration routes.

In some embodiments, a CSA-containing sporicidal composition is utilized to deactivate a dangerous substance or agent. For example, the sporicidal composition may be applied to a composition known or suspected as harboring dangerous bacterial spores, such as spores of the bacterium *Bacillus anthracis*. Such hazardous spores, or substances known or suspected as harboring such spores, may beneficially be deactivated or made less potent through the application of a CSA-containing sporicidal composition.

In some embodiments, a sporicidal composition is utilized to sterilize industrial equipment, such as pipes, containers, tanks, reactors, surfaces, and the like. In industrial food processing, for example, bacterial spores are often attracted to surfaces of pipes, tanks, and other equipment, where they can multiply and resporulate, leading to contamination of contacted food processed with the equipment. In some circumstances, typical treatments such as pasteurization are insufficient to kill bacterial spores and instead work to eliminate competition from other vegetative bacteria.

In some embodiments, a sporicidal composition as described herein kills or deactivates bacterial spores without requiring the addition of heat (e.g., without requiring autoclaving, ultrahigh-temperature (UHT) processing, or other such treatments). In other embodiments, heat may be utilized in conjunction with application of a sporicidal composition having CSAs. Beneficially, use of CSA-containing sporicidal compositions in combination with heat treatment may achieve a given level of spore killing/deactivation at temperatures lower than if heat treatment alone is used. In other words, a CSA-containing sporicidal composition may be utilized to augment a heat treatment process to achieve higher sporicidal activity and/or to achieve similar sporicidal activity at lower required temperatures.

Similarly, some embodiments may include the use of an acid, oxidizing agent, gamma radiation, or other sporicidal treatment in combination with use of a CSA-containing sporicidal composition. In such implementations, the CSA-containing sporicidal composition may be utilized to augment the sporicidal treatment to achieve higher sporicidal activity and/or to achieve similar sporicidal activity with lower levels of treatment acid, oxidizer, or radiation, for example.

In some embodiments, the one or more CSA compounds are included by weight in the sporicidal composition at about 0.1%, 0.5%, 1%, 3%, 5%, 10%, 15%, 20%, 25%, or 30% or are included by weight within a range defined by any two of the foregoing percentage values. In some embodiments, the one or more CSA compounds are included at a concentration of about 1 μg/ml, 5 μg/ml, 10 μg/ml, 25 μg/ml, 50 μg/ml, 100 μg/ml, 150 μg/ml, or 200 μg/ml, or are included at a concentration within a range defined by any two of the foregoing concentration values.

As explained above, when use of a CSA-containing sporicidal composition is combined with another sporicidal treatment, such as heat treatment, the amount or concentration of CSAs can be lowered while still providing the same sporicidal effect. Thus, in some implementations, the concentration of the CSA molecules is provided according to a sliding scale based on the temperature and/or based on the intensity of the other coinciding sporicidal treatment.

For example, for applications in which the sporicidal composition is utilized at about room temperature, the one or more CSA compounds may be provided at a concentration of about 10 μg/ml to about 200 μg/ml, or about 50 μg/ml to about 150 μg/ml, or about 100 μg/ml. For applications in which the sporicidal composition is utilized at about 70° C., the one or more CSA compounds may be provided at a concentration of about 1 μg/ml to about 40 μg/ml, or about 10 μg/ml to about 30 μg/ml, or about 20 μg/ml. At different temperatures, the one or more CSA compounds may be provided at concentrations determined by interpolating or extrapolating based on the foregoing values. For example, because a temperature of about 45° C. is about half way between room temperature (RT) and 70° C., the one or more CSA compounds may be provided at a concentration of about 40 μg/ml to about 80 μg/ml, or about 60 μg/ml.

It will be understood that in the foregoing examples, the upper concentration endpoints do not necessarily represent a lack of effectiveness at CSA concentrations beyond the upper endpoints. Rather, the upper range endpoints define ranges for which effective sporicidal activity may be achieved without the need for additional CSA compounds, thereby making efficient use of CSA compounds and associated formulation costs. In some implementations, such as where cost efficiency is less important than ensuring sporicidal activity, the one or more CSA compounds may be included at concentrations higher than the foregoing ranges.

Sporicidal compositions may include a suitable carrier in combination with the one or more CSA compounds. Suitable carriers may include, for example, water, saline, detergent solutions, liposome solutions, alcohols, oils, organic solvents, organic/aqueous emulsions, and combinations thereof. Sporicidal compositions may be formulated as liquid solutions, gels, pastes, foams, dry powders, washes, or other suitable form according to particular application needs.

III. Examples

Example 1

This example studied the ability of a CSA compound (e.g., CSA-13) to kill sporulated bacterial, namely *Bacillus subtilis* ATCC 6051 spores. To prepare *Bacillus subtilis* ATCC 6051 spores, bacteria were grown on LB (Luria-Bertani) agar plates without antibiotics at 37° C. for 72 h. Bacteria were harvested, re-suspended in ice-cold phosphate buffered saline (PBS) solution and purified by triple centrifugation (12 000×g, 10 min, 4° C.). The spore suspension was heat treated (75° C., 15 min) to remove remaining vegetative cells, cooled, stored in water at 4° C. and protected from light until analysis. Previous studies confirmed that heat activation with subsequent cooling does not significantly affect the properties of spores and their resistance to external factors. Zhang, P., P. Setlow, and Y. Li, *Characterization of single heat-activated Bacillus spores using laser tweezers Raman spectroscopy*. Opt Express, 2009. 17(19): p. 16480-91. All spores used in this work were free of vegetative cells (>98%), as determined by staining cells using Schaeffer and Fulton Spore Stain Kit (Sigma-Aldrich, St Louis, Mo., USA). Additionally, to confirm the formation of spores during preparation, purified samples were investigated using transmission electron microscopy (TEM, Tecnai G2 X-TWIN, FEI, USA).

As can be seen in FIG. 3, TEM micrographs confirmed the presence of *B. subtilis* spores with characteristic spore-exclusive structures (FIG. 3, panel B). As shown in FIG. 3, disruption of spore membrane architecture is shown after treatment with 50 μg/mL of CSA-13 at RT (panel C), and at 70° C. (panel D), and 200 μg/mL of CSA-13 at RT (panel E), and at 70° C. (panel F). Arrows indicate changes in membrane structure upon treatment with CSA-13.

Example 2

A viability assay of bacterial spores in the presence of a CSA compound was performed according to the protocol presented by Ghosh and Setlow. Ghosh, S. and P. Setlow, *Isolation and characterization of superdormant spores of Bacillus species*. J Bacteriol, 2009. 191(6): p. 1787-97. Spore suspensions in PBS were brought to 108 CFU/mL and incubated with various concentrations of CSA-13. To evaluate the effect of treatment time on the killing properties of the antibiotic, incubation was performed for 15, 30, 60, 120 and 240 min, respectively. To investigate the effect of temperature on sporicidal properties, incubation at room temperature (RT) and at 70° C. was performed. After incubation, the plates were transferred to ice and suspensions were diluted 10- to 1000-fold in PBS. Then, 10 µL aliquots were spotted on LB agar plates for overnight culture at 37° C. and CFUs were determined. Cell survival, after exposure to the tested agent, was expressed as percent of control.

Figure 4:
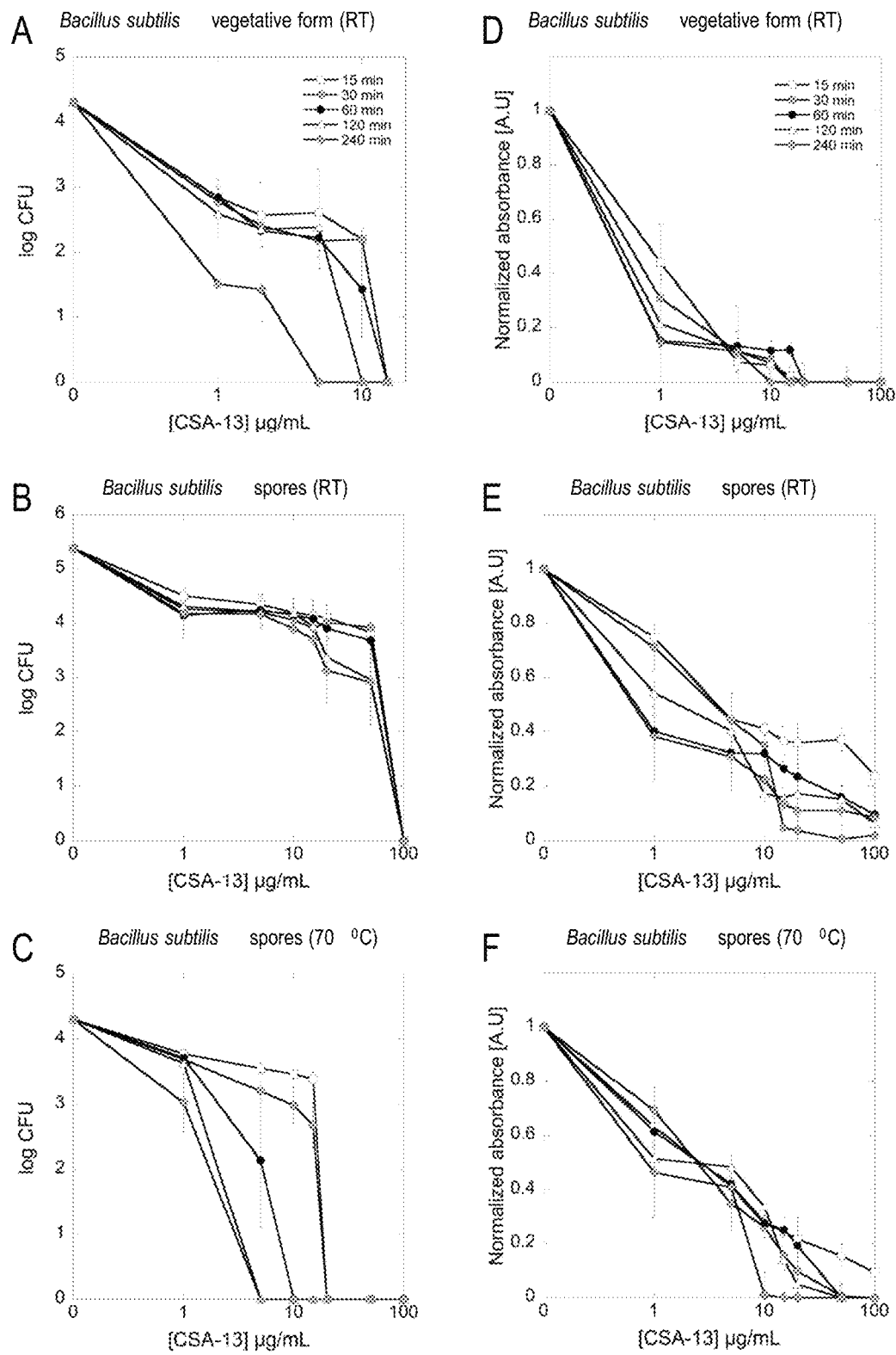
FIG. 4 includes graphs showing decreased survival of CSA-13-treated *B. subtilis* spores.

FIG. 4 includes graphs showing decreased survival of CSA-13-treated B. subtilis spores. FIG. 4, panels A-C show decline in the survival of B. subtilis culture after incubation with various concentrations of CSA-13. FIG. 4, panels D-F show Level of metabolic activity observed in ceragenin (CSA)-treated spore samples exposed to appropriate environmental conditions when compared to untreated control. Samples were incubated at RT (panels A, D for vegetative form and panels B, E for spore form, respectively) and at 70° C. (panels C, F) for 15 (white squares), 30 (grey circles), 60 (black circles), 120 (white triangles) and 240 (grey diamonds) minutes. The data was generated from experiments performed in triplicate.

As shown in FIG. 4, panel A, CSA-13 exerts high antibacterial activity against the vegetative form of B. subtilis at concentrations ranging from 1 to 15 µg/mL. Simultaneously, incubation of CSA-13 with spore suspension results in total inhibition of their growth potential at 100 µg/mL, as presented in FIG. 4, panel B. To assess whether the time of incubation significantly affects CSA-13 killing properties, incubation was extended to 4 h. Interestingly, the impact of incubation time was minimal; all vegetative cells were killed at a CSA-13 concentration of 15 µg/mL when incubation time reached 240 min. At the end point of the experiment, similar effects for spore cultures of bacteria were observed. Regardless of the incubation time, the dose of 100 µg/mL was shown to inhibit spore growth.

To assess the impact of higher temperature on spore viability, we performed additional incubations of spore suspensions with CSA-13 at 70° C. Spore survival after this treatment is shown in FIG. 4, panel C. It was confirmed that elevated temperature significantly intensifies the activity of CSA-13. In contrast to samples treated at room temperature, time- and dose-dependent effects during incubation in higher temperature were observed. Incubation lasting 15 min was sufficient to inhibit the growth of spores at a CSA-13 concentration of 20 µg/mL. Extension of incubation time to 120 and 240 minutes allowed the killing of bacterial spores at 5 µg/mL of CSA-13. At the same time, detection of metabolic activity in treated samples confirms low level of spores which were able to germinate in the presence of antibiotic.

Example 3

As an additional confirmation of results, the presence of a metabolically active fraction of cells was investigated using MTT assay. After incubation of spores with various concentrations of CSA-13 in a non-growing medium (PBS), 20 µL of MTT solution (thiazolyl blue tetrazolium bromide, Sigma-Aldrich, St Louis, Mo., USA, 5 mg/mL) and 100 µL of LB medium broth were added. Incubation at 37° C. was continued for 8 h. Medium was removed, and 100 µL of dimethyl sulfoxide solution (DMSO) was added to dissolve the MTT precipitate. Cells were allowed to stand at room temperature (RT) for 10 min with shaking. Absorbance values were detected at a wavelength of 570 nm using a microplate spectrophotometer. Absorbance values obtained in control spores cultures (without a tested agent) were taken as 100%. As positive controls, 1 M HCl (for spore treatment at RT) and 70% ethanol (for spore treatment at 70° C.) were employed. The average of all the experiments was presented in comparison to the level of metabolic activity detected in non-treated B. subtilis suspension. Incubation of both vegetative cells and spores of B. subtilis was performed for 15, 30, 60, 120 and 240 min.

The results of viability testing largely correlate with data obtained in the MTT assay. It has been established that dormant spores of Bacillus species exhibit low metabolism due to poor enzyme activity in the spore core and produce low levels of compounds such as NADH or ATP. However, the reactivation of spores and their return to vegetative metabolism, when the environmental conditions are suitable, is usually possible. The incubation of non-treated spores in LB broth at 37° C. results in reactivation of metabolic activity confirmed by increasing formazan reduction and subsequent rise in an absorbance value. Considering this fact, an additional test, allowing for detection of any metabolic activity in CSA-13-treated samples, was performed.

According to collected data, in samples treated with corresponding doses of CSA-13, almost no metabolic activity was present. Vegetative cells showed no detectable metabolism when subjected to incubation with CSA-13 at 20 µg/mL, which indicates strong antimicrobial activity of this agent against vegetative form of bacteria (FIG. 4, panel D). Importantly, only a small fraction of spores was able to resume proper metabolic activity after exposure to favorable environmental conditions (FIG. 4, panel E, and 4, panel F). These results show that CSA-13 strongly interferes the germination of B. subtilis spores.

Example 4

To further assess germination processes in antibiotic-treated samples, a spectrophotometric method was employed. Isolated spores were incubated at RT for 1 h in PBS with concentrations of CSA-13 ranging from 10 to 100 µg/mL. Then 100 µL of LB broth was added, and optical densities at 600 nm ($OD_{600}$) were monitored, using a microplate reader (Synergy H1, BioTek, VT, USA), for 60 min.

Figure 5:
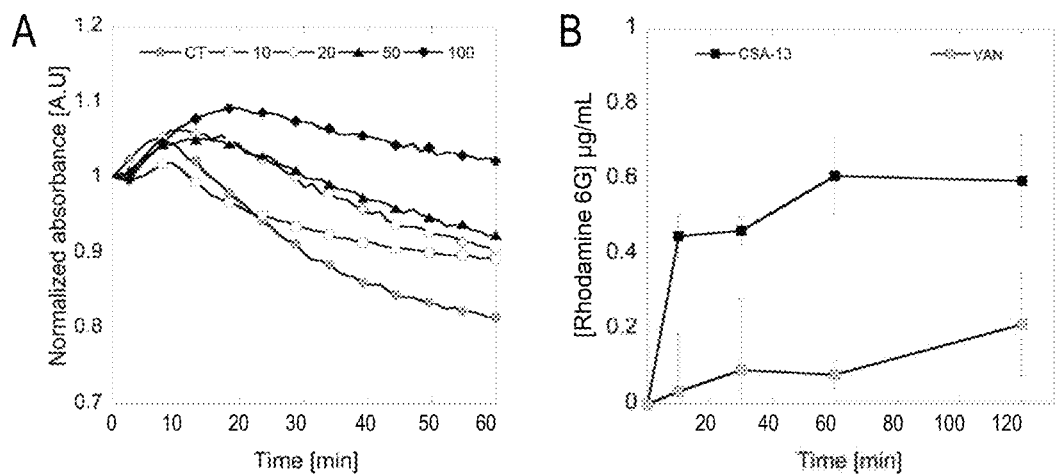
FIG. 5 includes graphs showing inhibitory effect of CSA-13 on *B. subtilis* spore germination.

FIG. 5 includes graphs showing inhibitory effect of CSA-13 on B. subtilis spore germination assessed by the measurement of optical density for spore suspension with increasing concentrations of the antibiotic (10 µg/mL—white squares; 20 µg/mL—white diamonds; 50 µg/mL—black triangles; 100 µg/mL—black diamonds), when compared with control (CT—grey circles) (panel A). Release of rhodamine 6G from external layers of B. subtilis spores after treatment with 20 µg/ml of CSA-13 (black square) and vancomycin (VAN; grey square) (panel B).

CSA-13's strong interference in the germination of B. subtilis spores was shown by measurement of optical density at 600 nm (OD600). The dose-dependent effects of CSA-13 on OD600 are shown in FIG. 5, panel A.

Example 5

The release of rhodamine 6G absorbed on the surface of Bacillus spores was evaluated using the Maesaki method (Maesaki, S., et al., Rhodamine 6G efflux for the detection of CDR1-overexpressing azole-resistant Candida albicans strains. J Antimicrob Chemother, 1999. 44(1): p. 27-31) with minor modifications. To stain cells with rhodamine 6G, the dye was added to a final concentration of 10 µM for 10 min. Non-absorbed dye was removed by centrifugation for 2 min at 10 000×g. Next, stained cells were washed and CSA-13 at 20 µg/mL was added. After incubation for 10, 30, 60 and 120 min, supernatant was collected by centrifugation and absorption at 527 nm was measured. The total concentration of rhodamine 6G released from the surface of spores was calculated using a standard concentration curve. The level of antibiotic-induced release was presented as the difference between the concentration of rhodamine 6G released from treated spores and control samples.

As shown in FIG. 5, panel B, treatment with CSA-13 at a dose of 20 µg/mL resulted in the release of dye, which strongly suggests the existence of a ceragenin-spore surface interactions. Notably, this effect was significantly higher than that of vancomycin. An additional assay employing FITC-labeled CSA-13 confirmed that CSA-13 exerts high affinity for the external layers of B. subtilis spores.

Example 6

To assess the affinity/binding of CSA-13 for the outer bacterial membrane, CSA-13 was labeled with fluorescein isothiocyanate (FITC) and added to the suspensions of vegetative cell and spores, to a final concentration of 20 µg/mL. The affinity of CSA-13 to cell membranes was assessed using fluorimetric measurement (Synergy H1, BioTek, VT, USA) with excitation/emission wavelengths of 298/534 nm recorded for 15 min. To evaluate whether affinity of CSA-13 is influenced by the surface electrical properties of cells, zeta potentials of vegetative bacteria and spore suspensions were assessed using Zetasizer Nano ZS (Malvern Instruments, United Kingdom). Bacterial and spore cultures were brought to $OD_{600}$~0.1 in PBS buffer (pH=7). To evaluate the effect of the ceragenin on zeta potential value, CSA-13 was added at the concentration of 100 µg/mL to the spore suspension, incubated for 15 minutes and transferred to a cuvette. Measurements were conducted at 25° C.

Figure 6:
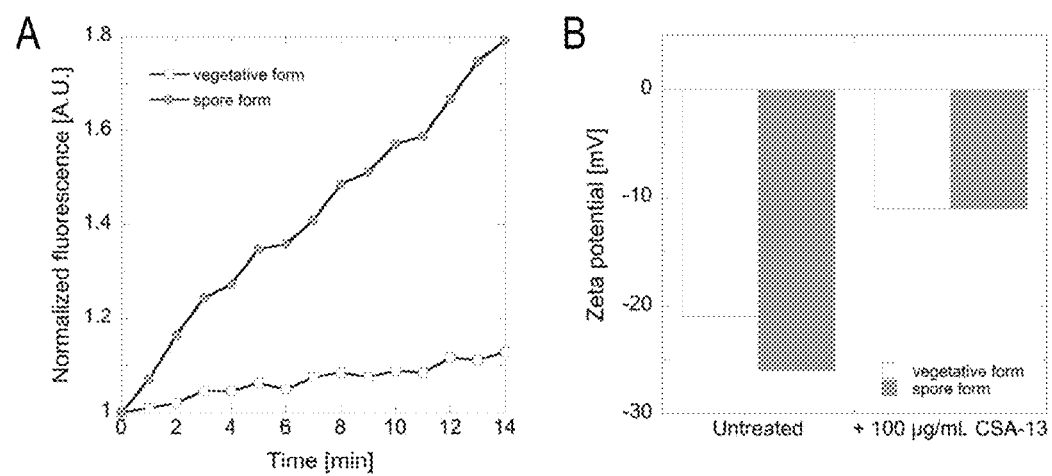
FIG. 6 includes graphs showing affinity of FITC-labeled CSA-13 to membrane of vegetative and spore form of *B. subtilis* and changes in zeta potential values of ceragenin-treated vegetative and spore of *B. subtilis*.

FIG. 6, panel A, is a graph showing affinity of FITC-labeled CSA-13 to membrane of vegetative and spore form of B. subtilis. FIG. 6, panel B, shows changes in zeta potential values of ceragenin-treated vegetative and spore of B. subtilis. Interestingly, CSA-13 possessed greater affinity for the spores than for the vegetative form of bacteria (FIG. 6, panel A). To investigate the cause of this effect, the zeta-potential of B. subtilis in vegetative and spore forms was measured (FIG. 6, panel B). It was confirmed that spores possess more negative surface charge (−26 mV) than vegetative cells (−21 mV), which is the most likely cause of the differences in interactions with positively charged molecules such as CSA-13. Additionally, incubation of samples with 100 µg/mL CSA-13 led to a decrease in the absolute value of the observed zeta-potential (−11 mV).

Example 7

To visualize alterations in morphology and membrane permeability of treated spores, a suspension of spores ($OD_{600}$~0.5) in distilled water was treated with CSA-13 at concentrations of 50 µg/mL and 200 µg/mL and incubated for 1 hour at RT and 70° C. TEM Micrographs of treated spores were made using Tecnai G2 X-TWIN (FEI, Oregon, USA).

Figure 3:
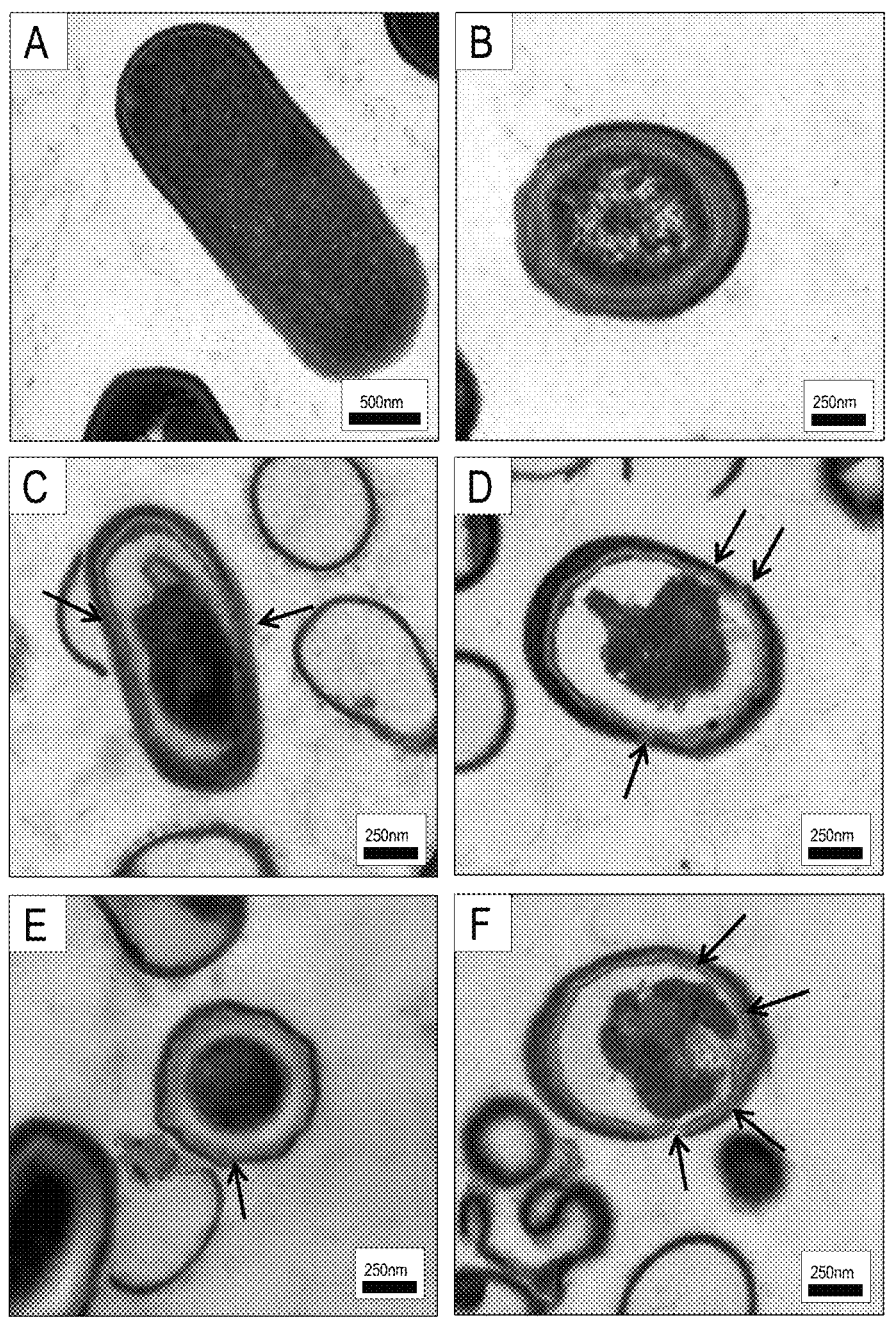
FIG. 3 shows TEM micrographs of untreated vegetative (panel A) and spore form of *B. subtilis* (panel B), and treated sport form (panels C, D, E, F).

Resulting micrographs clearly illustrate that CSA-13 affects spore structure (FIG. 3, panels C-F). Both local and extensive changes in the integrity of external layers of spore lead to alternations within the spore core, which suggests that CSA-13 not only affects the structure of the spore coat but also increases the permeability of the outer and inner spore membranes. In particular, the ability of CSA-13 to bypass the impermeability of spore's inner membrane is considered as vital for the action of this agent, considering that maintained integrity of this layer plays a crucial role in the development of spore resistance to many chemicals. Additionally, considerable alternations in the structure of DNA-consisting spore core suggest that CSA-13 treatment might also cause DNA damage or change of its condensation resulting in cell death.

Example 8

For Raman spectroscopy analyses, spores of B. subtilis were suspended in 100 µL of distilled water and treated with CSA-13 (50 µg/mL and 200 µg/mL) for 1 hour at RT and 70° C. Samples were transferred to polished calcium fluoride ($CaF_2$) optical windows (Crystran, United Kingdom) and dried at 60° C. Raman spectra were recorded using a Renishaw InVia Raman spectrometer equipped with an optical confocal microscope, an air-cooled laser emitting at 532 nm, and an CCD detector thermoelectrically cooled to −70° C. A dry Leica N PLAN EPI (100×, NA 0.85) objective was used. The power of the laser at the sample position was ca. 1.5 mW. A sum of 20 scans with integration time of 20 seconds and a resolution of 0.5 $cm^{-1}$ was collected. The spectrometer was calibrated using the Raman scattering line generated by an internal silicon plate. A laser spot (diameter of ca. 760 nm) was focused on a single spore and then the measurement was performed. All spectra were smoothed and baseline corrected. Results from one representative experiment are provided.

DPA is considered to be one the key factors determining the resistance of B. subtilis spores to UV radiation and desiccation and as one of the molecules involved in the protection of DNA from damage. Additionally, the release of this molecule occurs during killing of spores by wet heat and is preceded by an increase in inner membrane permeability. Confocal Raman spectroscopy was used for analysis of changes in the chemical composition of spores upon treatment with CSA-13

Figure 7:
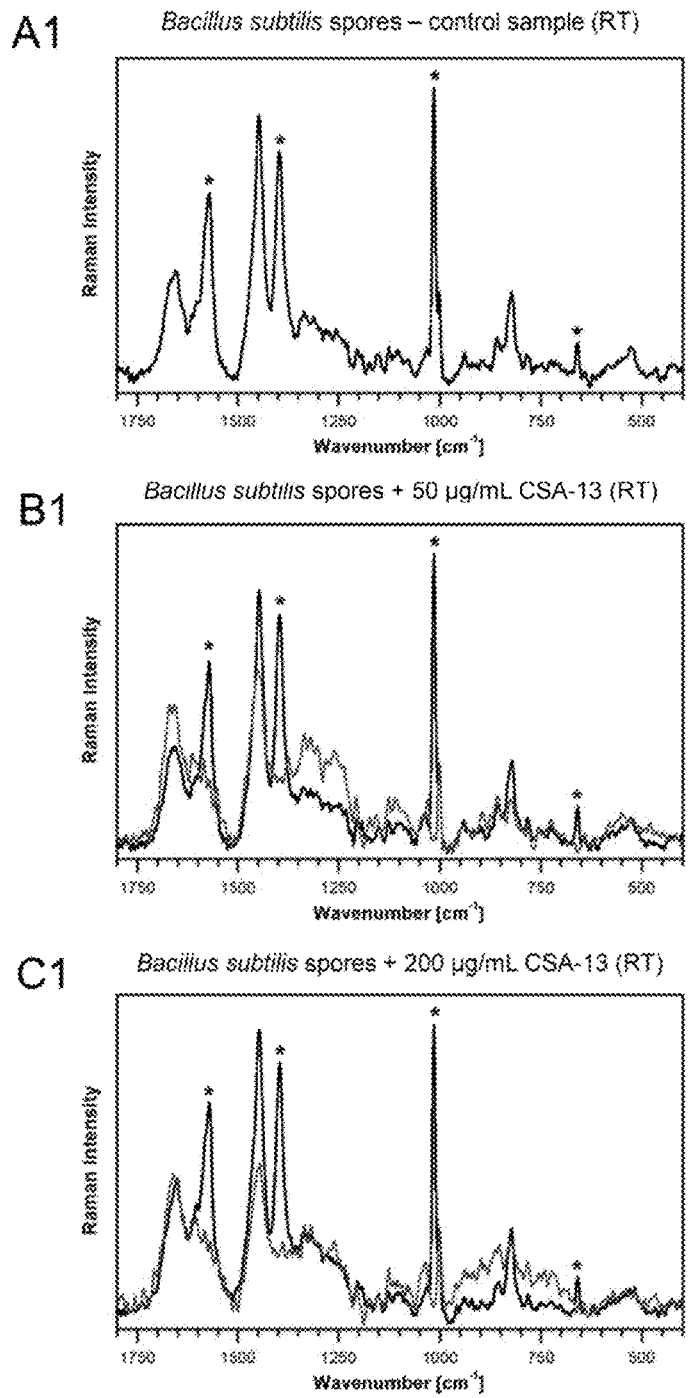
FIGS. 7 and 8 show Raman spectra collected from *B. subtilis* spores incubated at RT and at 70° C., respectively, with corresponding confocal microscopy images.
Figure 7:
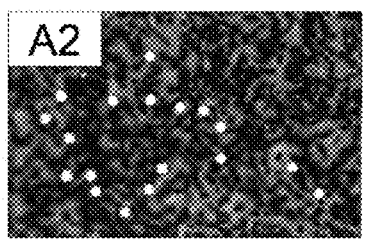
Figure 7:
Figure 7:
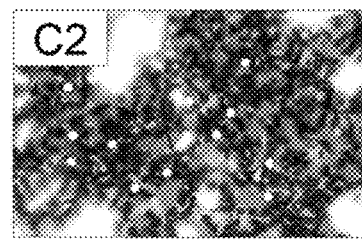
Figure 8:
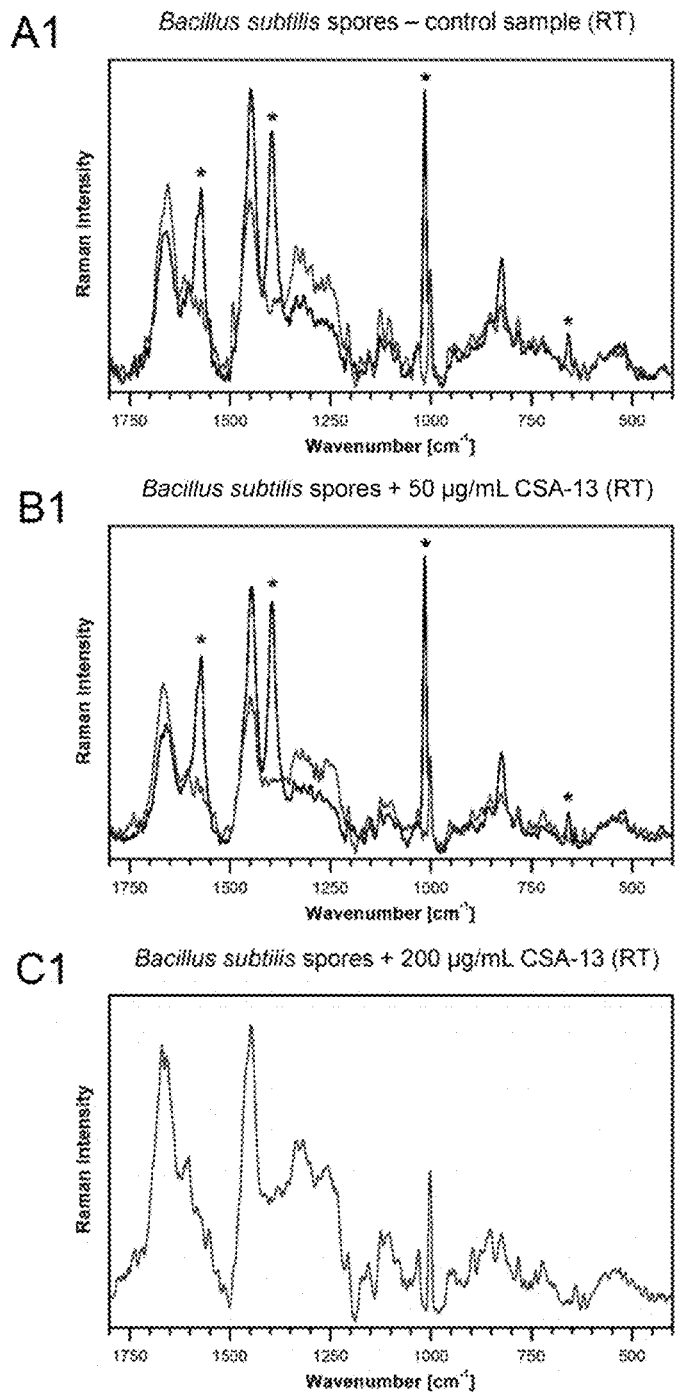
Figure 8:
Figure 8:
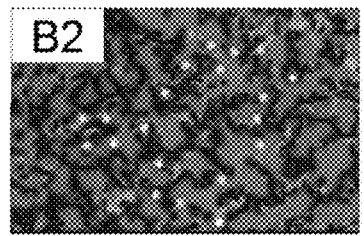
Figure 8:
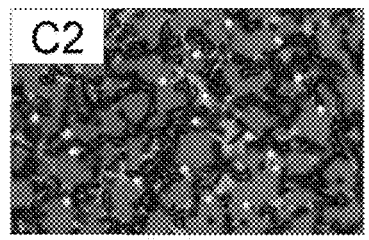

FIGS. 7 and 8 show Raman spectra collected from B. subtilis spores incubated at RT and at 70° C., respectively, with corresponding confocal microscopy images. Panels A1 and A2—control sample, panels B1 and B2—50 µg/mL of CSA-13, panels C1 and C2—200 µg/mL of CSA-13. Asterisks denote CaDPA bands well separated from bands of spore biocomponents. Blue color indicates CaDPA negative spore, while red color indicates CaDPA positive spores. Spectra were normalized to the 1002 $cm^{-1}$ band.

DPA forms a complex with divalent ions (mostly $Ca^{2+}$) and this complex exhibits characteristic bands in Raman spectra. The presence of these bands in spectra obtained from a single spore can be interpreted as high-CaDPA content cell (CaDPA positive), while their absence as low or undetectable CaDPA content cell (CaDPA negative). Following this approach, CSA-13 treated and untreated spores underwent spectroscopic evaluation. Based on Raman spectra it was shown that incubation of spores with the ceragenin resulted in a significant reduction of the number of CaDPA positive cells, while almost all untreated cells contained this complex. When treatment was conducted at 70° C., the percentage of CaDPA negative spores was greater compared to sample treated at room temperature (FIG. 8). This effect correlates with observed increase of CSA-13 sporicidal activity at 70° C.

IV. Additional Details of CSA Compounds

More specific examples of CSA compounds according to Formula I are shown below in Formulas II and III, wherein Formula III differs from Formula II by omitting $R_{15}$ and the ring carbon to which it is attached. The R groups shown in the Formulae can have a variety of different structures. CSA compounds, and a variety of different R groups, useful in accordance with the present disclosure, are disclosed in U.S. Pat. Nos. 6,350,738, 6,486,148, 6,767,904, 7,598,234, 7,754,705, 8,975,310, and 9,434,759, which are incorporated herein by reference.

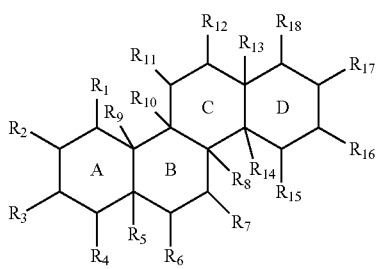

(II)

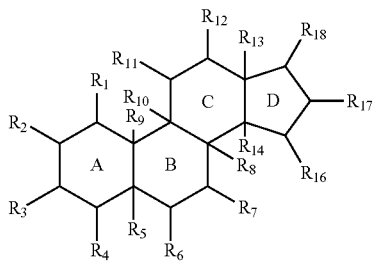

(II)

In some embodiments of Formulas II and III, at least two of $R_3$, $R_7$, and $R_{12}$ may independently include a cationic moiety (e.g., amino or guanidino groups) bonded to the steroid backbone structure via a non-hydrolysable or hydrolysable linkage. For the embodiments of the present disclosure, the linkage is preferably non-hydrolysable under conditions of sterilization and storage, and physiological conditions. Such cationic functional groups (e.g., amino or guanidino groups) may be separated from the backbone by at least one, two, three, four or more atoms.

Optionally, a tail moiety may be attached to the backbone structures at $R_{18}$. The tail moiety may have variable chain length or size and may be charged, uncharged, polar, non-polar, hydrophobic, amphipathic, and the like. The tail moiety may, for example, be configured to alter the hydrophobicity/hydrophilicity of the ceragenin compound. CSA compounds of the present disclosure having different degrees of hydrophobicity/hydrophilicity may, for example, have different rates of uptake into different target microbes.

The R groups described herein, unless specified otherwise, may be substituted or unsubstituted.

In some embodiments shown by Formulas II and III:
each of fused rings A, B, C, and D may be independently saturated, or may be fully or partially unsaturated, provided that at least two of A, B, C, and D is saturated, wherein rings A, B, C, and D form a ring system. Other ring systems can also be used, e.g., 5-member fused rings and/or compounds with backbones having a combination of 5- and 6-membered rings;

$R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, alkyl, hydroxyalkyl, alkyloxyalkyl, alkylcarboxyalkyl, alkylaminoalkyl, alkylaminoalkylamino, alkylaminoalkylamino-alkylamino, aminoalkyl, aryl, arylaminoalkyl, haloalkyl, alkenyl, alkynyl, oxo, a linking group attached to a second steroid, aminoalkyloxy, aminoalkyloxyalkyl, aminoalkylcarboxy, aminoalkylaminocarbonyl, aminoalkylcarboxamido, di(alkyl)aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—$HC(Q_5)$-$C(O)$—$O$—, guanidinoalkyloxy, quaternary ammonium alkylcarboxy, and guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{18}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, alkyl, hydroxyalkyl, alkyloxyalkyl, aminoalkyl, aryl, haloalkyl, alkenyl, alkynyl, oxo, a linking group attached to a second steroid, aminoalkyloxy, aminoalkylcarboxy, aminoalkylaminocarbonyl, di(alkyl)aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—$HC(Q_5)$-$C(O)$—$O$—, guanidinoalkyloxy, and guanidinoalkyl-carboxy, where $Q_5$ is a side chain of any amino acid, P.G. is an amino protecting group.

In some embodiments, at least one, and sometimes two or three of $R_{1-4}$, $R_6$, $R_7$, $R_{11}$, $R_{12}$, $R_{15}$, $R_{16}$, $R_{17}$, and $R_{18}$ are independently selected from the group consisting of aminoalkyl, aminoalkyloxy, alkyl carboxyalkyl, alkyl aminoalkyl amino, alkyl aminoalkylaminoalkylamino, aminoalkylcarboxy, arylaminoalkyl, aminoalkyloxyaminoalkylamino-carbonyl, aminoalkylaminocarbonyl, aminoalkyl-carboxyamido, a quaternary ammonium alkylcarboxy, di(alkyl)aminoalkyl, $H_2N$—$HC(Q_5)$-$C(O)$—$O$—, $H_2N$—$HC(Q_5)$-$C(O)$—$N(H)$—, azidoalkyloxy, cyanoalkyloxy, P.G.-HN—$HC(Q_5)$-$C(O)$—$O$—, guanidine-alkyloxy, and guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, $(C_1$-$C_{22})$ alkyl, $(C_1$-$C_{22})$ hydroxyalkyl, $(C_1$-$C_{22})$ alkyloxy-$(C_1$-$C_{22})$ alkyl, $(C_1$-$C_{22})$ alkylcarboxy-$(C_1$-$C_{22})$ alkyl, $(C_1$-$C_{22})$ alkylamino-$(C_1$-$C_{22})$ alkyl, $(C_1$-$C_{22})$ alkylamino-$(C_1$-$C_{22})$ alkylamino, $(C_1$-$C_{22})$ alkylamino-$(C_1$-$C_{22})$ alkylamino-$(C_1$-$C_{22})$ alkylamino, $(C_1$-$C_{22})$ aminoalkyl, aryl, arylamino-$(C_1$-$C_{22})$ alkyl, $(C_1$-$C_{22})$ haloalkyl, $C_2$-$C_6$ alkenyl, $C_2$-$C_6$ alkynyl, oxo, a linking group attached to a second steroid, $(C_1$-$C_{22})$ aminoalkyloxy, $(C_1$-$C_{22})$ aminoalkyloxy-$(C_1$-$C_{22})$ alkyl, $(C_1$-$C_{22})$ aminoalkylcarboxy, $(C_1$-$C_{22})$ aminoalkylaminocarbonyl, $(C_1$-$C_{22})$ aminoalkyl-carboxamido, di($C_1$-$C_{22}$ alkyl)aminoalkyl, $H_2N$—$HC(Q_5)$-$C(O)$—$O$—, $H_2N$—$HC(Q_5)$-$C(O)$—$N(H)$—, $(C_1$-$C_{22})$ azidoalkyloxy, $(C_1$-$C_{22})$ cyanoalkyloxy, P.G.-HN—$HC(Q_5)$-$C(O)$—$O$—, $(C_1$-$C_{22})$ guanidinoalkyloxy, $(C_1$-$C_{22})$ quaternary ammonium alkylcarboxy, and $(C_1$-$C_{22})$ guanidinoalkyl carboxy, where $Q_5$ is a side chain of an amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, $(C_1$-$C_{22})$ alkyl, $(C_1$-$C_{22})$ hydroxyalkyl, $(C_1$-$C_{22})$ alkyloxy-$(C_1$-$C_{22})$ alkyl, $(C_1$-$C_{22})$ aminoalkyl, aryl, $(C_1$-$C_{22})$ haloalkyl, $(C_2$-$C_6)$ alkenyl, $(C_2$-$C_6)$ alkynyl, oxo, a linking group attached to a second steroid, $(C_1$-$C_{22})$ aminoalkyloxy, $(C_1$-$C_{22})$ aminoalkylcarboxy, $(C_1$-$C_{22})$ aminoalkylaminocarbonyl, di($C_1$-$C_{22}$ alkyl)aminoalkyl, $H_2N$—$HC(Q_5)$-$C(O)$—$O$—, $H_2N$—$HC(Q_5)$-$C(O)$—$N(H)$—, $(C_1$-$C_{22})$ azidoalkyloxy, $(C_1$-$C_{22})$ cyanoalkyloxy, P.G.-HN—HC($Q_5$)-C(O)—O—, ($C_1$-$C_{22}$) guanidinoalkyloxy, and ($C_1$-$C_{22}$) guanidinoalkylcarboxy, where $Q_5$ is a side chain of any amino acid, and P.G. is an amino protecting group;

provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of ($C_1$-$C_{22}$) aminoalkyl, ($C_1$-$C_{22}$) aminoalkyloxy, ($C_1$-$C_{22}$) alkylcarboxy-($C_1$-$C_{22}$) alkyl, ($C_1$-$C_{22}$) alkylamino-($C_1$-$C_{22}$) alkylamino, ($C_1$-$C_{22}$) alkylamino-($C_1$-$C_{22}$) alkylamino ($C_1$-$C_{22}$) alkylamino, ($C_1$-$C_{22}$) aminoalkylcarboxy, arylamino ($C_1$-$C_{22}$) alkyl, ($C_1$-$C_{22}$) aminoalkyloxy ($C_1$-$C_{22}$) aminoalkylaminocarbonyl, ($C_1$-$C_{22}$) aminoalkylaminocarbonyl, ($C_1$-$C_{22}$) aminoalkyl carboxyamido, ($C_1$-$C_{22}$) quaternary ammonium alkylcarboxy, di($C_1$-$C_{22}$ alkyl) aminoalkyl, $H_2N$—HC($Q_5$)-C(O)—O—, $H_2N$—HC($Q_5$)-C(O)—N(H)—, ($C_1$-$C_{22}$) azidoalkyloxy, ($C_1$-$C_{22}$) cyanoalkyloxy, P.G.-HN—HC($Q_5$)-C(O)—O—, ($C_1$-$C_{22}$) guanidinoalkyloxy, and ($C_1$-$C_{22}$) guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, ($C_1$-$C_{18}$) alkyl, ($C_1$-$C_{18}$) hydroxyalkyl, ($C_1$-$C_{18}$) alkyloxy-($C_1$-$C_{18}$) alkyl, ($C_1$-$C_{18}$) alkylcarboxy-($C_1$-$C_{18}$) alkyl, ($C_1$-$C_{18}$) alkylamino-($C_1$-$C_{18}$) alkyl, ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, ($C_1$-$C_{18}$) aminoalkyl, aryl, arylamino-($C_1$-$C_{18}$) alkyl, oxo, ($C_1$-$C_{18}$) aminoalkyloxy, ($C_1$-$C_{18}$) aminoalkyloxy-($C_1$-$C_{18}$) alkyl, ($C_1$-$C_{18}$) aminoalkylcarboxy, ($C_1$-$C_{18}$) aminoalkylaminocarbonyl, ($C_1$-$C_{18}$) aminoalkyl-carboxamido, di($C_1$-$C_{18}$ alkyl)aminoalkyl, ($C_1$-$C_{18}$) guanidinoalkyloxy, ($C_1$-$C_{18}$) quaternary ammonium alkylcarboxy, and ($C_1$-$C_{18}$) guanidinoalkyl carboxy; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, ($C_1$-$C_{18}$) alkyl, ($C_1$-$C_{18}$) hydroxyalkyl, ($C_1$-$C_{18}$) alkyloxy-($C_1$-$C_{18}$) alkyl, ($C_1$-$C_{18}$) alkylcarboxy-($C_1$-$C_{18}$) alkyl, ($C_1$-$C_{18}$) alkylamino-($C_1$-$C_{18}$)alkyl, ($C_1$-$C_{18}$) alkylamino-($C_1$-$C_{18}$) alkylamino, ($C_1$-$C_{18}$) alkylamino-($C_1$-$C_{18}$) alkylamino-($C_1$-$C_{18}$) alkylamino, ($C_1$-$C_{18}$) aminoalkyl, aryl, arylamino-($C_1$-$C_{18}$) alkyl, oxo, ($C_1$-$C_{18}$) aminoalkyloxy, ($C_1$-$C_{18}$) aminoalkyloxy-($C_1$-$C_{18}$) alkyl, ($C_1$-$C_{18}$) aminoalkylcarboxy, ($C_1$-$C_{18}$) aminoalkylaminocarbonyl, ($C_1$-$C_{18}$) aminoalkylcarboxamido, di($C_1$-$C_{18}$ alkyl)aminoalkyl, ($C_1$-$C_{18}$) guanidinoalkyloxy, ($C_1$-$C_{18}$) quaternary ammonium alkylcarboxy, and ($C_1$-$C_{18}$) guanidinoalkyl carboxy, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of of hydrogen, hydroxyl, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted aryl, an unsubstituted arylamino-($C_1$-$C_{18}$) alkyl, oxo, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkylaminocarbonyl, an unsubstituted ($C_1$-$C_{18}$) aminoalkylcarboxamido, an unsubstituted di($C_1$-$C_{18}$ alkyl)aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy.

In some embodiments, $R_3$, $R_7$, $R_{12}$, and $R_{18}$ are independently selected from the group consisting of hydrogen, an unsubstituted ($C_1$-$C_{18}$) alkyl, unsubstituted ($C_1$-$C_{18}$) hydroxyalkyl, unsubstituted ($C_1$-$C_{18}$) alkyloxy-($C_1$-$C_{18}$) alkyl, unsubstituted ($C_1$-$C_{18}$) alkylcarboxy-($C_1$-$C_{18}$) alkyl, unsubstituted ($C_1$-$C_{18}$) alkylamino-($C_1$-$C_{18}$)alkyl, unsubstituted ($C_1$-$C_{18}$) alkylamino-($C_1$-$C_{18}$) alkylamino, unsubstituted ($C_1$-$C_{18}$) alkylamino-($C_1$-$C_{18}$) alkylamino-($C_1$-$C_{18}$) alkylamino, an unsubstituted ($C_1$-$C_{18}$) aminoalkyl, an unsubstituted arylamino-($C_1$-$C_{18}$) alkyl, an unsubstituted ($C_1$-$C_{18}$) aminoalkyloxy, an unsubstituted ($C_1$-$C_{18}$) aminoalkyloxy-($C_1$-$C_{18}$) alkyl, an unsubstituted ($C_1$-$C_{18}$) aminoalkylcarboxy, an unsubstituted ($C_1$-$C_{18}$) aminoalkyl aminocarbonyl, an unsubstituted ($C_1$-$C_{18}$) aminoalkylcarboxamido, an unsubstituted di($C_1$-$C_{18}$ alkyl) aminoalkyl, unsubstituted ($C_1$-$C_{18}$) guanidinoalkyloxy, unsubstituted ($C_1$-$C_{18}$) quaternary ammonium alkylcarboxy, and unsubstituted ($C_1$-$C_{18}$) guanidinoalkyl carboxy. In some embodiments, $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted ($C_1$-$C_6$) alkyl.

In some embodiments, $R_3$, $R_7$, $R_{12}$, and $R_{18}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy.

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonyloxyalkyl; di(alkyl)aminoalkyl; alkylcarboxyalkyl; and hydroxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; alkylcarboxyalkyl; and hydroxyalkyl.

In some embodiments, $R_3$, $R_7$, and $R_{12}$ are the same.

In some embodiments, $R_3$, $R_7$, and $R_{12}$ are aminoalkyloxy.

In some embodiments, $R_{18}$ is alkylaminoalkyl.

In some embodiments, $R_{18}$ is alkoxycarbonylalkyl.

In some embodiments, $R_{18}$ is di(alkyl)aminoalkyl.

In some embodiments, $R_{18}$ is alkylcarboxyalkyl.

In some embodiments, $R_{18}$ is hydroxyalkyl.

In some embodiments, $R_3$, $R_7$, and $R_{12}$ are aminoalkylcarboxy.

In some embodiments, $R_3$, $R_7$, $R_{12}$, and $R_{18}$ are independently selected from the group consisting of aminoalkyloxy; aminoalkylcarboxy; alkylaminoalkyl; di-(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy, and wherein $R_{18}$ is selected from the group consisting of alkylaminoalkyl; di-(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy, and wherein $R_{18}$ is selected from the group consisting of alkylaminoalkyl; di-(alkyl)aminoalkyl; and alkoxycarbonylalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; $C_{10}$-alkoxy-carbonyl-$C_4$-alkyl; $C_6$-alkyl-carboxy-$C_4$-alkyl; $C_8$-alkyl-carboxy-$C_4$-alkyl; and $C_{10}$-alkyl-carboxy-$C_4$-alkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; and $C_{10}$-alkoxy-carbonyl-$C_4$-alkyl.

In some embodiments, $R_3$, $R_7$, and $R_{12}$, are independently selected from the group consisting of amino-$C_3$-alkyloxy or amino-$C_3$-alkyl-carboxy, and wherein $R_{18}$ is selected from the group consisting of $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; $C_{10}$-alkoxy-carbonyl-$C_4$-alkyl; $C_6$-alkyl-carboxy-$C_4$-alkyl; $C_8$-alkyl-carboxy-$C_4$-alkyl; and $C_{10}$-alkyl-carboxy-$C_4$-alkyl.

In some embodiments, $R_3$, $R_7$, and $R_{12}$, are independently selected from the group consisting of amino-$C_3$-alkyloxy or amino-$C_3$-alkyl-carboxy, and wherein $R_{18}$ is selected from the group consisting of $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; and $C_{10}$-alkoxy-carbonyl-$C_4$-alkyl.

In some embodiments, $R_3$, $R_7$, $R_{12}$, and $R_{18}$ are independently selected from the group consisting of amino-$C_3$-alkyloxy; amino-$C_3$-alkyl-carboxy; amino-$C_2$-alkylcarboxy; $C_8$-alkylamino-$C_5$-alkyl; $C_8$-alkoxy-carbonyl-$C_4$-alkyl; $C_{10}$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; $C_{16}$-alkylamino-$C_5$-alkyl; $C_{12}$-alkylamino-$C_5$-alkyl; and hydroxy($C_5$)alkyl.

In some embodiments, $R_{18}$ is selected from the group consisting of $C_8$-alkylamino-$C_5$-alkyl or $C_8$-alkoxy-carbonyl-$C_4$-alkyl.

In some embodiments, at least $R_{18}$ can have the following structure:

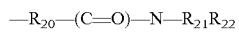

wherein $R_{20}$ is omitted or alkyl, alkenyl, alkynyl, or aryl, and $R_{21}$ and $R_{22}$ are independently selected from the group consisting of hydrogen, alkyl, alkenyl, alkynyl, or aryl, provided that at least one of $R_{21}$ and $R_{22}$ is not hydrogen.

In some embodiments, $R_{21}$ and $R_{22}$ are independently selected from the group consisting of hydrogen, $C_1$-$C_{24}$ alkyl, $C_2$-$C_{24}$ alkenyl, $C_2$-$C_{24}$ alkynyl, $C_6$ or $C_{10}$ aryl, 5 to 10 membered heteroaryl, 5 to 10 membered heterocyclyl, $C_7$-$C_{13}$ aralkyl, (5 to 10 membered heteroaryl)-$C_1$-$C_6$ alkyl, $C_3$-$C_{10}$ carbocyclyl, $C_{4-10}$ (carbocyclyl)alkyl, (5 to 10 membered heterocyclyl)-$C_1$-$C_6$ alkyl, amido, and a suitable amine protecting group, provided that at least one of $R_{21}$ and $R_{22}$ is not hydrogen. In some embodiments, $R_{21}$ and $R_{22}$, together with the atoms to which they are attached, form a 5 to 10 membered heterocyclyl ring.

In some embodiments, one or more of rings A, B, C, and D is heterocyclic.

In some embodiments, rings A, B, C, and D are non-heterocyclic.

In some embodiments, the CSA compound is a compound of Formula IV, which is a subset of Formula III, or salt thereof, having a steroidal backbone:

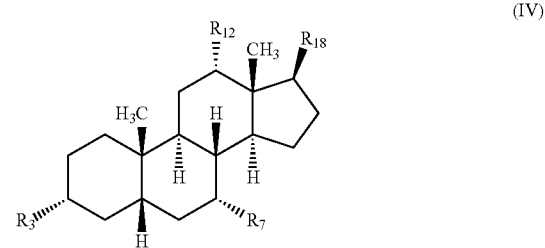

(IV)

In some embodiments, $R_3$, $R_7$, and $R_{12}$ are independently selected from the group consisting of hydrogen, an unsubstituted ($C_1$-$C_{22}$) alkyl, unsubstituted ($C_1$-$C_{22}$) hydroxyalkyl, unsubstituted ($C_1$-$C_{22}$) alkyloxy-($C_1$-$C_{22}$) alkyl, unsubstituted ($C_1$-$C_{22}$) alkylcarboxy-($C_1$-$C_{22}$) alkyl, unsubstituted ($C_1$-$C_{22}$) alkylamino-($C_1$-$C_{22}$)alkyl, unsubstituted ($C_1$-$C_{22}$) alkylamino-($C_1$-$C_{22}$) alkylamino, unsubstituted ($C_1$-$C_{22}$) alkylamino-($C_1$-$C_{22}$) alkylamino-($C_1$-$C_{18}$) alkylamino, an unsubstituted ($C_1$-$C_{22}$) aminoalkyl, an unsubstituted arylamino-($C_1$-$C_{22}$) alkyl, an unsubstituted ($C_1$-$C_{22}$) aminoalkyloxy, an unsubstituted ($C_1$-$C_{22}$) aminoalkyloxy-($C_1$-$C_{22}$) alkyl, an unsubstituted ($C_1$-$C_{22}$) aminoalkylcarboxy, an unsubstituted ($C_1$-$C_{22}$) aminoalkyl-aminocarbonyl, an unsubstituted ($C_1$-$C_{22}$) aminoalkylcarboxamido, an unsubstituted di($C_1$-$C_{22}$ alkyl)aminoalkyl, unsubstituted ($C_1$-$C_{22}$) guanidinoalkyloxy, unsubstituted ($C_1$-$C_{22}$) quaternary ammonium alkylcarboxy, and unsubstituted ($C_1$-$C_{22}$) guanidinoalkyl carboxy.

In some embodiments, $R_3$, $R_7$, and $R_{12}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$) alkyl, unsubstituted ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy.

In some embodiments, $R_3$, $R_7$, and $R_{12}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkylcarboxyalkyl; and hydroxyalkyl.

In some embodiments, $R_3$, $R_7$, and $R_{12}$ are independently selected from the group consisting of aminoalkyloxy and aminoalkylcarboxy.

In some embodiments, $R_3$, $R_7$, and $R_{12}$ are the same. In some embodiments, $R_3$, $R_7$, and $R_{12}$ are aminoalkyloxy. In some embodiments, $R_3$, $R_7$, and $R_{12}$ are aminoalkylcarboxy.

In some embodiments, $R_3$, $R_7$, and $R_{12}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

In some embodiments, CSA compounds as disclosed herein can be a compound of Formula I, Formula II, Formula III, Formula IV, or salts thereof wherein at least $R_{18}$ of the steroidal backbone includes amide functionality in which the carbonyl group of the amide is positioned between the amido nitrogen of the amide and fused ring D of the steroidal backbone. For example, any of the embodiments described above can substitute $R_{18}$ for an $R_{18}$ including amide functionality in which the carbonyl group of the amide is positioned between the amido nitrogen of the amide and fused ring D of the steroidal backbone.

In some embodiments, one or more of $R_3$, $R_7$, or $R_{12}$ may include a guanidine group as a cationic functional group and may be bonded to the steroid backbone by an ether linkage. For example, one or more of $R_3$, $R_7$, or $R_{12}$ may be a guanidinoalkyloxy group. An example includes $H_2N$—C(=NH)—NH-alkyl-O—,

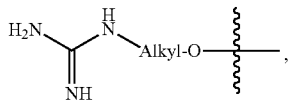

wherein the alkyl portion is defined as with the embodiments described above. In a preferred embodiment, the alkyl portion is a straight chain with 3 carbon atoms, and therefore one or more of $R_3$, $R_7$, or $R_{12}$ may be a guanidinopropyloxy group.

One of skill in the art will recognize that other cationic functional groups may be utilized, and that the cationic functional groups may be bonded to the steroid backbone through a variety of other tethers or linkages. For example, the cationic functional groups may be bonded to the steroid backbone by an ester linkage. For example, one or more of $R_3$, $R_7$, or $R_{12}$ may be an aminoalkylcarboxy or guanidinoalkylcarboxy, such as $H_2N$-alkyl-C(=O)—O— or $H_2N$—C(=NH)—NH-alkyl-C(=O)—O—, wherein the alkyl portion is defined as with the embodiments described above. In other embodiments, the cationic functional groups may be bonded to the steroid backbone by an amide linkage. For example, one or more of $R_3$, $R_7$, or $R_{12}$ may be an aminoalkylcarbonylamino (i.e. aminoalkylcarboxamido) or guanidinoalkylcarbonylamino (i.e. guanidinoalkylcarboxamido), such as $H_2N$-alkyl-C(=O)—NH— or $H_2N$—C(=NH)—NH-alkyl-C(=O)—NH—, wherein the alkyl portion is defined as with the embodiments described above.

Additionally, one of skill in the art will recognize that the tethers may be of varying lengths. For example, the length between the steroid backbone and the cationic functional group (e.g., amino or guanidino group), may be between 1 and 15 atoms or even more than 15 atoms. In other embodiments, the length may be between 1 and 8 atoms. In a preferred embodiment, the length of the tether is between two and four atoms. In other embodiments, there is no tether, such that the cationic functional group is bonded directly to the steroid backbone.

One of skill in the art will also note that the various cationic functional groups of the present disclosure may be utilized in combination, such that one or more of $R_3$, $R_7$, or $R_{12}$ may include one variation of cationic functional group while one or more of another of $R_3$, $R_7$, or $R_{12}$ of the same compound may include a different variation of cationic functional group. Alternatively, two or more of $R_3$, $R_7$, or $R_{12}$ may include the same cationic functional group, or all of $R_3$, $R_7$, or $R_{12}$ may include the same cationic functional group (in embodiments where all of $R_3$, $R_7$, or $R_{12}$ are cationic functional groups).

Additionally, although in a preferred embodiment one or more cationic functional groups are disposed at $R_3$, $R_7$, or $R_{12}$, one of skill in the art will recognize that in other embodiments, $R_3$, $R_7$, or $R_{12}$ may not be cationic functional groups and/or one or more cationic functional groups may be disposed at other locations of the steroid backbone. For example, one or more cationic functional groups may be disposed at $R_1$, $R_2$, $R_3$, $R_4$, $R_6$, $R_7$, $R_{11}$, $R_{12}$, $R_{15}$, $R_{16}$, $R_{17}$, and/or $R_{18}$.

The compounds and compositions disclosed herein are optionally prepared as salts. The term "salt" as used herein is a broad term, and is to be given its ordinary and customary meaning to a skilled artisan (and is not to be limited to a special or customized meaning), and refers without limitation to a salt of a compound. In some embodiments, the salt is an acid addition salt of the compound. Salts can be obtained by reacting a compound with inorganic acids such as hydrohalic acid (e.g., hydrochloric acid or hydrobromic acid), sulfuric acid, nitric acid, and phosphoric acid. Salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the salt is a hydrochloride salt. In some embodiments, the salt is a mono-hydrochloride salt, a di-hydrochloride salt, a tri-hydrochloride salt, or a tetra-hydrochloride salt. Additional examples of salts include sulfuric acid addition salts, sulfonic acid addition salts, disulfonic acid addition salts, 1,5-naphthalenedisulfonic acid addition salts, sulfate salts, and bisulfate salts.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of killing or deactivating bacterial spores on one or more objects, the method including:
    applying a sporicidal composition having one or more cationic steroidal antimicrobial (CSA) compounds to the one or more objects; and
    the sporicidal composition killing or deactivating one or more bacterial spores contacting the sporicidal composition,
    wherein the sporicidal composition is applied to the one or more objects in conjunction with heat treatment of the one or more objects.

2. The method of claim 1, wherein the sporicidal composition further comprises a carrier selected from the group consisting of water, alcohol, oil, organic solvent, organic/aqueous emulsion, and combinations thereof.

3. The method of claim 1, wherein the sporicidal composition is non-oxidizing.

4. The method of claim 1, wherein the sporicidal composition has a pH of between about 6 and 8.

5. The method of claim 1, wherein the one or more objects comprise one or more food products.

6. The method of claim 5, further comprising reducing spoilage and/or extending shelf life of the one or more food products relative to similar food products not treated with the sporicidal composition.

7. The method of claim 1, wherein the one or more objects comprise food processing equipment.

8. The method of claim 1, wherein the one or more objects comprise one or more medical devices.

9. The method of claim 1, wherein the sporicidal composition is applied to a hazardous substance known or suspected as including hazardous bacterial spores.

10. The method of claim 1, wherein the one or more CSA compounds are provided at concentration that varies according to a temperature at which the sporicidal composition is utilized.

11. The method of claim 1, wherein the one or more CSA compounds includes CSA-13.

12. The method of claim 1, wherein the one or more CSA compounds are provided at a concentration of about 1 µg/ml to about 200 µg/ml.

13. The method of claim 12, wherein the one or more CSA compounds are provided at a concentration of about 1 µg/ml to about 150 µg/ml.

14. The method of claim 12, wherein the one or more CSA compounds are provided at a concentration of about 1 µg/ml to less than 100 µg/ml.

15. The method of claim 1, wherein the sporicidal composition functions to increase permeability of bacterial spore inner membranes.

16. A method of killing or deactivating bacterial spores on one or more objects, the method including:
    applying a sporicidal composition having one or more cationic steroidal antimicrobial (CSA) compounds to the one or more objects; and
    the sporicidal composition killing or deactivating one or more bacterial spores of at least one *Bacillus* or *Clostridium* species contacting the sporicidal composition,
    wherein the sporicidal composition is applied to the one or more objects in conjunction with heat treatment of the one or more objects.

17. The method of claim 16, the sporicidal composition killing or deactivating one or more bacterial spores of *Clostridium difficile*.

18. A method of killing or deactivating bacterial spores on one or more objects, the method including:
    applying a sporicidal composition having one or more cationic steroidal antimicrobial (CSA) compounds provided at a concentration of about 10 µg/ml to about 200 µg/ml to the one or more objects and/or into air in contact with the one or more objects; and
    the sporicidal composition killing or deactivating one or more bacterial spores contacting the sporicidal composition,
    wherein the sporicidal composition is applied to the one or more objects in conjunction with heat treatment of the one or more objects.

19. The method of claim 18, wherein the one or more CSA compounds includes CSA-13.

* * * * *